United States Patent
Verweij et al.

(10) Patent No.: US 12,123,001 B2
(45) Date of Patent: Oct. 22, 2024

(54) METHODS OF TREATING LIVER DISEASES WITH PHOSPHODIESTERASE 3B (PDE3B) INHIBITORS

(71) Applicant: Regeneron Pharmaceuticals, Inc., Tarrytown, NY (US)

(72) Inventors: Niek Verweij, Tarrytown, NY (US); Olukayode Sosina, Tarrytown, NY (US); Parsa Akbari, Tarrytown, NY (US); Adam Locke, Tarrytown, NY (US); Aris Baras, Tarrytown, NY (US); Luca Andrea Lotta, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 193 days.

(21) Appl. No.: 17/740,382

(22) Filed: May 10, 2022

(65) Prior Publication Data

US 2022/0364099 A1 Nov. 17, 2022

Related U.S. Application Data

(60) Provisional application No. 63/186,838, filed on May 11, 2021.

(51) Int. Cl.
*C12N 15/113* (2010.01)
*A61P 1/16* (2006.01)
*A61P 3/10* (2006.01)
*C12Q 1/6883* (2018.01)

(52) U.S. Cl.
CPC ............ *C12N 15/1137* (2013.01); *A61P 1/16* (2018.01); *A61P 3/10* (2018.01); *C12Q 1/6883* (2013.01); *C12N 2310/11* (2013.01); *C12N 2310/14* (2013.01); *C12N 2310/531* (2013.01); *C12N 2320/30* (2013.01); *C12Q 2600/106* (2013.01); *C12Q 2600/156* (2013.01)

(58) Field of Classification Search
CPC ............ C12N 15/1137; C12N 2310/11; C12N 2310/14; C12N 2310/531; C12N 2320/30; C12N 2310/20; C12N 2320/34; A61P 1/16; A61P 3/10; C12Q 1/6883; C12Q 2600/106; C12Q 2600/156; A61K 31/7088; A61K 31/7105; A61K 45/06; C12Y 301/04017
USPC ...................................................... 514/44 A
See application file for complete search history.

(56) References Cited

U.S. PATENT DOCUMENTS

2007/0249668 A1* 10/2007 Sprague ............. A61P 3/00
424/94.1

FOREIGN PATENT DOCUMENTS

| JP | 2009242378 | 10/2009 | |
|---|---|---|---|
| WO | 2002070469 | 9/2002 | |
| WO | WO-2005030787 A2 * | 4/2005 | ............. C07H 21/00 |
| WO | 2009008539 | 1/2009 | |
| WO | 2011111066 | 9/2011 | |
| WO | 2016079652 | 5/2016 | |
| WO | 2020010181 | 1/2020 | |
| WO | WO-2020010181 A1 * | 1/2020 | ......... A61K 31/4709 |
| WO | 2021160131 | 8/2021 | |

OTHER PUBLICATIONS

Amarapurkar DN. Prescribing medications in patients with decompensated liver cirrhosis. Int J Hepatol. 2011;2011:519526 (Year: 2011).*
Tang Y.et al., Improvement in insulin resistance and the restoration of reduced phosphodiesterase 3B gene expression by pioglitazone in adipose tissue of obese diabetic KKAy mice.Diabetes. 1999; 48: 1830-1835 (Year: 1999).*
Berger, K., et al., (2009). Phosphodiesterase 3B is localized in caveolae and smooth ER in mouse hepatocytes and is important in the regulation of glucose and lipid metabolism. PloS one, 4(3), e4671 (Year: 2009).*
Choi YH, et al., Alterations in regulation of energy homeostasis in cyclic nucleotide phosphodiesterase 3B-null mice. J Clin Invest. Dec. 2006;116(12):3240-51 (Year: 2006).*
Emdin, C.A., Khera, A.V., Chaffin, M. et al. Analysis of predicted loss-of-function (pLOF) variants in UK Biobank identifies variants protective for disease. Nat Commun 9, 1613 (2018) (Year: 2018).*
Movsesian M, Ahmad F, Hirsch E. Functions of PDE3 Isoforms in Cardiac Muscle. J Cardiovasc Dev Dis. Feb. 6, 2018;5(1):10. (Year : 2018).*
Oh, Y. J., et al., (2018). Cilostazol Improves HFD-Induced Hepatic Steatosis by Upregulating Hepatic STAMP2 Expression through AMPK. Molecular pharmacology, 94(6), 1401-1411 (Year: 2018).*
Klarin, D., Damrauer, S.M., Cho, K. et al. Genetics of blood lipids among ~300,000 multi-ethnic participants of the Million Veteran Program. Nat Genet 50, 1514-1523 (2018) (Year: 2018).*
Chung et al., Targeted disruption of PDE3B, but not PDE3A, protects murine heart from ischemia/reperfusion injury, 2015, Proceedings of the National Academy of Sciences E2253-E2262, 112, 17 (Year: 2015).*
Guo et al., "Effects of Chinese Medicinal Formula BNG-1 on Phosphodiesterase 3B Expression, Hepatic Steatosis, and Insulin Resistance in High Fat Diet-induced NAFLD Mice", International Journal of Medical Science, 2018, 15(11), pp. 1194-1202.
An et al., "The Loss-of-Function S267F Variant in HBV Receptor NTCP Reduces Human Risk for HBV Infection and Disease Progression", Journal of Infectious Diseases, 2018, 218(9), pp. 1404-1410.
Scott et al., "Genetics of alcoholic liver disease and non-alcoholic steatohepatitis", Clinical Medicine, 2018, 17(18), pp. s54-s59.
Klarin et al., "Genetics of blood lipids among ~300,000 multi-ethnic participants of the Million Veteran Program", Nature Genetics, 2018, 50(11), pp. 1514-1523.

* cited by examiner

Primary Examiner — Neil P Hammell
Assistant Examiner — Shabana S Meyering
(74) Attorney, Agent, or Firm — Armstrong Teasdale LLP

(57) ABSTRACT

The present disclosure provides methods of treating a subject having a liver disease or type 2 diabetes, and methods of identifying subjects having an increased risk of developing a liver disease or type 2 diabetes.

14 Claims, No Drawings

Specification includes a Sequence Listing.

METHODS OF TREATING LIVER DISEASES WITH PHOSPHODIESTERASE 3B (PDE3B) INHIBITORS

REFERENCE TO SEQUENCE LISTING

This application includes a Sequence Listing submitted electronically as a text file named 18923806901SEQ, created on May 9, 2022, with a size of 1,081,598 bytes. The Sequence Listing is incorporated herein by reference.

FIELD

The present disclosure relates generally to the treatment of subjects having a liver disease with Phosphodiesterase 3B (PDE3B) inhibitors, and methods of identifying subjects having an increased risk of developing a liver disease.

BACKGROUND

Chronic liver disease and cirrhosis are leading causes of morbidity and mortality in the United States accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of subjects awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

The global epidemic of Type 2 diabetes (T2D) is a major public health problem, as this disease is the fifth leading cause of death worldwide and a leading cause of morbidity, premature coronary heart disease, stroke, peripheral vascular disease, renal failure, and amputation. The number of individuals living with diabetes worldwide is predicted to increase from 366 million in 2011 to 552 million by 2030.

T2D is characterized by hyperglycemia due to impaired insulin secretion and insulin resistance in target tissues. T2D is typically diagnosed after age 40 years and is caused by the combined action of genetic susceptibility and environmental factors. T2D is associated with obesity, and it is also a polygenic disease.

Phosphodiesterase 3B (PDE3B) is a member of a family of phosphohydrolyases that catalyze the hydrolysis of 3' cyclic phosphate bonds in adenosine and/or guanine 3',5' cyclic monophosphate (cAMP and/or cGMP), which results in the formation of the respective nucleoside 5' monophosphates. The cyclic nucleotides cAMP and cGMP serve as second messengers in a number of cellular signaling pathways. The PDEs as well as the guanylyl and adenylyl cyclases, which synthesize the cyclic nucleotides, are cellular components to regulate the concentration of cyclic nucleotides and, thus, to regulate the signal transduction pathways. In particular, PDEs regulate the second messengers by controlling their degradation.

SUMMARY

The present disclosure provides methods of treating a subject having a liver disease, or having a risk for developing a liver disease, or who have risk factors for developing a liver disease, or who have a risk of developing complications of a liver disease, the methods comprising administering a PDE3B inhibitor to the subject.

The present disclosure also provides methods of treating a subject having a fatty liver disease, or having a risk for developing a fatty liver disease, or who have risk factors for developing a fatty liver disease, or who have a risk of developing complications of a fatty liver disease, the methods comprising administering a PDE3B inhibitor to the subject.

The present disclosure also provides methods of treating a subject having hepatocellular carcinoma, or having a risk for developing hepatocellular carcinoma, or who have risk factors for developing hepatocellular carcinoma, or who have a risk of developing complications of hepatocellular carcinoma, the methods comprising administering a PDE3B inhibitor to the subject.

The present disclosure also provides methods of treating a subject having liver cirrhosis, or having a risk for developing liver cirrhosis, or who have risk factors for developing liver cirrhosis, or who have a risk of developing complications of liver cirrhosis, the methods comprising administering a PDE3B to the subject.

The present disclosure also provides methods of treating a subject having liver fibrosis, or having a risk for developing liver fibrosis, or who have risk factors for developing liver fibrosis, or who have a risk of developing complications of liver fibrosis, the methods comprising administering a PDE3B inhibitor to the subject.

The present disclosure also provides methods of treating a subject having simple steatosis, steatohepatitis, or non-alcoholic steatohepatitis (NASH), or having a risk for developing simple steatosis, steatohepatitis, or NASH, or who have risk factors for developing simple steatosis, steatohepatitis, or NASH, or who have a risk of developing complications of simple steatosis, steatohepatitis, or NASH, the methods comprising administering a PDE3B inhibitor to the subject.

The present disclosure also provides methods of treating a subject having a liver injury, or having a risk for developing a liver injury, or who have risk factors for developing a liver injury, or who have a risk of developing complications of a liver injury, the methods comprising administering a PDE3B inhibitor to the subject.

The present disclosure also provides methods of treating a subject having type 2 diabetes, or having a risk for developing type 2 diabetes, or who have risk factors for developing type 2 diabetes, or who have a risk of developing complications of type 2 diabetes, the methods comprising administering a PDE3B inhibitor to the subject.

The present disclosure also provides methods of treating a subject with a therapeutic agent that treats or inhibits a liver disease or type 2 diabetes, wherein the subject is suffering from a liver disease or type 2 diabetes, the methods comprising the steps of: determining whether the subject has a PDE3B predicted loss-of-function or missense variant nucleic acid molecule encoding a human PDE3B polypeptide by: obtaining or having obtained a biological sample from the subject; and performing or having performed a sequence analysis on the biological sample to determine if the subject has a genotype comprising the PDE3B predicted loss-of-function or missense variant nucleic acid molecule;

when the subject is heterozygous for a PDE3B predicted loss-of-function or missense variant nucleic acid molecule, then administering or continuing to administer to the subject the therapeutic agent that treats or inhibits the liver disease or type 2 diabetes in an amount that is the same as or less than a standard dosage amount, and administering to the subject a PDE3B inhibitor; and when the subject is homozygous for a PDE3B predicted loss-of-function or missense variant nucleic acid molecule, then administering or continuing to administer to the subject the therapeutic agent that treats or inhibits the liver disease or type 2 diabetes in an amount that is the same as or less than a standard dosage amount; and when the subject is PDE3B reference, then administering or continuing to administer to the subject the therapeutic agent that treats or inhibits the liver disease or type 2 diabetes in an amount that is greater than a standard dosage amount, and administering to the subject a PDE3B inhibitor; wherein the presence of a genotype having the PDE3B predicted loss-of-function or missense variant nucleic acid molecule encoding the human PDE3B polypeptide indicates the subject has a decreased risk of developing the liver disease or type 2 diabetes.

The present disclosure also provides methods of identifying a subject having an increased risk of developing a liver disease or type 2 diabetes, wherein the methods comprise: determining or having determined the presence or absence of a PDE3B predicted loss-of-function or missense variant nucleic acid molecule encoding a human PDE3B polypeptide in a biological sample obtained from the subject; wherein: when the subject is PDE3B reference, then the subject has an increased risk of developing the liver disease or type 2 diabetes; and when the subject is heterozygous or homozygous for a PDE3B predicted loss-of-function or missense variant, then the subject has a decreased risk of developing the liver disease or type 2 diabetes.

The present disclosure also provides therapeutic agents that treat or inhibit a liver disease or type 2 diabetes for use in the treatment of the liver disease or type 2 diabetes in a subject that is PDE3B reference (in an amount that is greater than a standard dosage amount) or that has: a Phosphodiesterase 3B (PDE3B) predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide (in an amount that is less than or the same as a standard dosage amount).

The present disclosure also provides PDE3B inhibitors that treat or inhibit a liver disease or type 2 diabetes for use in the treatment of the liver disease or type 2 diabetes in a subject that is PDE3B reference or that is heterozygous for: a PDE3B predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that loss-of-function variants in PDE3B (whether these variations are homozygous or heterozygous in a particular subject) associate with a decreased risk of developing a liver disease or type 2 diabetes. It is believed that loss-of-function variants in the PDE3B gene or protein have not been associated with liver diseases or type 2 diabetes in genome-wide or exome-wide association studies. Therefore, subjects that are PDE3B reference or heterozygous for PDE3B variant nucleic acid molecules may be treated with a PDE3B inhibitor such that a liver disease or type 2 diabetes is inhibited, the symptoms thereof are reduced, and/or development of symptoms is repressed. It is also believed that such subjects having liver diseases or type 2 diabetes may further be treated with therapeutic agents that treat or inhibit a liver disease or type 2 diabetes.

For purposes of the present disclosure, any particular subject, such as a human, can be categorized as having one of three PDE3B genotypes: i) PDE3B reference; ii) heterozygous for a predicted loss-of-function or missense variant PDE3B nucleic acid molecule; or iii) homozygous for a predicted loss-of-function or missense variant PDE3B nucleic acid molecule. A subject is PDE3B reference when the subject does not have a copy of a PDE3B predicted loss-of-function or missense variant nucleic acid molecule. A subject is heterozygous for a PDE3B predicted loss-of-function or missense variant when the subject has a single copy of a PDE3B predicted loss-of-function or missense variant nucleic acid molecule. A PDE3B predicted loss-of-function or missense variant nucleic acid molecule is any nucleic acid molecule (such as, a genomic nucleic acid molecule, an mRNA molecule, or a cDNA molecule) encoding a variant PDE3B polypeptide having a partial loss-of-function, a complete loss-of-function, a predicted partial loss-of-function, or a predicted complete loss-of-function. A subject who has a PDE3B polypeptide having a partial loss-of-function (or predicted partial loss-of-function) is hypomorphic for PDE3B. A subject is homozygous for a PDE3B predicted loss-of-function or missense variant nucleic acid molecule when the subject has two copies (same or different) of a PDE3B predicted loss-of-function or missense variant nucleic acid molecule.

For subjects that are genotyped or determined to be PDE3B reference, such subjects have an increased risk of developing type 2 diabetes or a liver disease, such as, liver injury, liver cirrhosis, liver fibrosis, steatosis, steatohepatitis, or non-alcoholic steatohepatitis (NASH), liver inflammation, and/or fatty liver disease. For subjects that are genotyped or determined to be either PDE3B reference or heterozygous for a PDE3B predicted loss-of-function or missense variant, such subjects or subjects can be treated with a PDE3B inhibitor.

In any of the embodiments described herein, the PDE3B predicted loss-of-function or missense variant nucleic acid molecule can be any nucleic acid molecule (such as, for example, genomic nucleic acid molecule, mRNA molecule, or cDNA molecule) encoding a PDE3B variant polypeptide having a partial loss-of-function, a complete loss-of-function, a predicted partial loss-of-function, or a predicted complete loss-of-function. In some embodiments, the PDE3B predicted loss-of-function or missense variant nucleic acid molecule is associated with a reduced in vitro response to PDE3B ligands compared with reference PDE3B. In some embodiments, the PDE3B predicted loss-of-function or missense variant nucleic acid molecule is a PDE3B variant that results or is predicted to result in a premature truncation of a PDE3B polypeptide compared to the human reference genome sequence. In some embodiments, the PDE3B predicted loss-of-function or missense variant nucleic acid molecule is a variant that is predicted to be damaging by in vitro prediction algorithms such as Polyphen, SIFT, or similar algorithms. In some embodiments, the PDE3B predicted loss-of-function or missense variant nucleic acid molecule is a variant that causes or is predicted to cause a nonsynonymous amino-acid substitution in PDE3B and whose allele frequency is less than 1/100 alleles in the population from which the subject is selected. In some embodiments, the PDE3B predicted loss-of-function or missense variant nucleic acid molecule is any rare missense variant (allele frequency <0.1%; or 1 in 1,000 alleles), or any splice-site, stop-gain, start-loss, stop-loss, frameshift, or in-frame indel, or other frameshift PDE3B variant.

In any of the embodiments described herein, the PDE3B predicted loss-of-function polypeptide can be any PDE3B polypeptide having a partial loss-of-function, a complete loss-of-function, a predicted partial loss-of-function, or a predicted complete loss-of-function.

In any of the embodiments described herein, the PDE3B predicted loss-of-function or missense variant nucleic acid molecules encoding variations in the protein sequence can include variations at positions of chromosome 11 using the nucleotide sequence of the PDE3B reference genomic nucleic acid molecule (SEQ ID NO:1; ENSG00000152270.9 chr11:14,643,804-14,872,044 in the GRCh38/hg38 human genome assembly) as a reference sequence.

Numerous genetic variants in PDE3B exist which cause subsequent changes in the PDE3B polypeptide sequence including, but not limited to those listed in Table 1.

TABLE 1

PDE3B Genetic Variants (GRCh38/hg38 human genome assembly)

| Genomic coordinates for the genetic variant, C:P:R:A | Variant classified as pLOF | Transcript |
| --- | --- | --- |
| 11:14644077:T:G | Yes | ENST00000282096:ENST00000455098 |
| 11:14644077:T:C | Yes | ENST00000282096:ENST00000455098 |
| 11:14644078:G:C | Yes | ENST00000282096:ENST00000455098 |
| 11:14644078:G:A | Yes | ENST00000282096:ENST00000455098 |
| 11:14644095:ACG:A | Yes | ENST00000282096:ENST00000455098 |
| 11:14644141:GC:G | Yes | ENST00000282096:ENST00000455098 |
| 11:14644141:G:GC | Yes | ENST00000282096:ENST00000455098 |
| 11:14644153:T:TTA | Yes | ENST00000282096:ENST00000455098 |
| 11:14644196:C:T | Yes | ENST00000282096:ENST00000455098 |
| 11:14644270:T:TC | Yes | ENST00000282096:ENST00000455098 |
| 11:14644324:C:CGCCCT | Yes | ENST00000282096:ENST00000455098 |
| 11:14644378:G:A | Yes | ENST00000282096:ENST00000455098 |
| 11:14644395:G:A | Yes | ENST00000282096:ENST00000455098 |
| 11:14644396:G:A | Yes | ENST00000282096:ENST00000455098 |
| 11:14644415:G:GT | Yes | ENST00000282096:ENST00000455098 |
| 11:14644434:G:GC | Yes | ENST00000282096:ENST00000455098 |
| 11:14644531:G:A | Yes | ENST00000282096:ENST00000455098 |
| 11:14644534:G:A | Yes | ENST00000282096:ENST00000455098 |
| 11:14644560:AC:A | Yes | ENST00000282096:ENST00000455098 |

TABLE 1-continued

PDE3B Genetic Variants (GRCh38/hg38 human genome assembly)

| Genomic coordinates for the genetic variant, C:P:R:A | Variant classified as pLOF | Transcript |
|---|---|---|
| 11:14644582:G:A | Yes | ENST00000282096:ENST00000455098 |
| 11:14644601:T:TG | Yes | ENST00000282096:ENST00000455098 |
| 11:14644602:G:A | Yes | ENST00000282096:ENST00000455098 |
| 11:14644636:CA:C | Yes | ENST00000282096:ENST00000455098 |
| 11:14644795:GC:G | Yes | ENST00000282096:ENST00000455098 |
| 11:14644802:GC:G | Yes | ENST00000282096:ENST00000455098 |
| 11:14644830:T:TG | Yes | ENST00000282096:ENST00000455098 |
| 11:14644904:C:T | Yes | ENST00000282096:ENST00000455098 |
| 11:14644925:GA:G | Yes | ENST00000282096:ENST00000455098 |
| 11:14644930:AG:A | Yes | ENST00000282096:ENST00000455098 |
| 11:14645038:TA:T | Yes | ENST00000282096:ENST00000455098 |
| 11:14645048:G:T | Yes | ENST00000282096:ENST00000455098 |
| 11:14771972:TA:T | Yes | ENST00000282096:ENST00000455098 |
| 11:14771977:C:CTCAA | Yes | ENST00000282096:ENST00000455098 |
| 11:14771984:T:A | Yes | ENST00000282096:ENST00000455098 |
| 11:14771988:GT:G | Yes | ENST00000282096:ENST00000455098 |
| 11:14771988:G:T | Yes | ENST00000282096:ENST00000455098 |
| 11:14786526:AC:A | Yes | ENST00000282096:ENST00000455098 |
| 11:14786554:AT:A | Yes | ENST00000282096 |
| 11:14786634:CT:C | Yes | ENST00000282096 |
| 11:14786686:G:A | Yes | ENST00000282096 |
| 11:14789132:TC:T | Yes | ENST00000282096:ENST00000455098 |
| 11:14789136:C:T | Yes | ENST00000282096:ENST00000455098 |
| 11:14803942:A:T | Yes | ENST00000282096:ENST00000455098 |
| 11:14803943:G:T | Yes | ENST00000282096:ENST00000455098 |
| 11:14803943:G:C | Yes | ENST00000282096:ENST00000455098 |
| 11:14803958:TA:T | Yes | ENST00000282096:ENST00000455098 |
| 11:14803967:CT:C | Yes | ENST00000282096:ENST00000455098 |
| 11:14803982:TA:T | Yes | ENST00000282096:ENST00000455098 |
| 11:14804027:AC:A | Yes | ENST00000282096:ENST00000455098 |
| 11:14804036:GTC:G | Yes | ENST00000282096:ENST00000455098 |
| 11:14818182:G:C | Yes | ENST00000282096:ENST00000455098 |
| 11:14818182:G:A | Yes | ENST00000282096:ENST00000455098 |
| 11:14818244:TCTAA:T | Yes | ENST00000282096:ENST00000455098 |
| 11:14818245:C:CT | Yes | ENST00000282096:ENST00000455098 |
| 11:14818254:C:T | Yes | ENST00000282096:ENST00000455098 |
| 11:14818356:C:T | Yes | ENST00000282096:ENST00000455098 |
| 11:14818394:G:T | Yes | ENST00000282096:ENST00000455098 |
| 11:14819134:A:G | Yes | ENST00000282096:ENST00000455098 |
| 11:14819154:GA:G | Yes | ENST00000282096:ENST00000455098 |
| 11:14819165:C:A | Yes | ENST00000282096:ENST00000455098 |
| 11:14819171:CT:C | Yes | ENST00000282096:ENST00000455098 |
| 11:14830697:G:A | Yes | ENST00000282096:ENST00000455098 |
| 11:14830728:C:A | Yes | ENST00000282096:ENST00000455098 |
| 11:14830764:CAG:C | Yes | ENST00000282096:ENST00000455098 |
| 11:14830773:AAGAC:A | Yes | ENST00000282096:ENST00000455098 |
| 11:14830835:C:T | Yes | ENST00000282096:ENST00000455098 |
| 11:14830838:C:T | Yes | ENST00000282096:ENST00000455098 |
| 11:14831639:G:C | Yes | ENST00000282096:ENST00000455098 |
| 11:14831639:G:T | Yes | ENST00000282096:ENST00000455098 |
| 11:14831649:G:T | Yes | ENST00000282096:ENST00000455098 |
| 11:14831659:TG:T | Yes | ENST00000282096:ENST00000455098 |
| 11:14831679:G:T | Yes | ENST00000282096:ENST00000455098 |
| 11:14831689:C:A | Yes | ENST00000282096:ENST00000455098 |
| 11:14831729:TG:T | Yes | ENST00000282096:ENST00000455098 |
| 11:14831757:TC:T | Yes | ENST00000282096:ENST00000455098 |
| 11:14831769:CTCAG:C | Yes | ENST00000282096:ENST00000455098 |
| 11:14831771:C:CA | Yes | ENST00000282096:ENST00000455098 |
| 11:14832719:TA:T | Yes | ENST00000282096:ENST00000455098 |
| 11:14832742:AG:A | Yes | ENST00000282096:ENST00000455098 |
| 11:14832805:AT:A | Yes | ENST00000282096:ENST00000455098 |
| 11:14832809:GA:G | Yes | ENST00000282096:ENST00000455098 |
| 11:14832818:TATC:T | Yes | ENST00000282096:ENST00000455098 |
| 11:14832821:C:T | Yes | ENST00000282096:ENST00000455098 |
| 11:14832827:A:AT | Yes | ENST00000282096:ENST00000455098 |
| 11:14832831:C:CT | Yes | ENST00000282096:ENST00000455098 |
| 11:14832833:TGTAA:T | Yes | ENST00000282096:ENST00000455098 |
| 11:14832835:T:A | Yes | ENST00000282096:ENST00000455098 |
| 11:14835096:GT:G | Yes | ENST00000282096:ENST00000455098 |
| 11:14835097:T:C | Yes | ENST00000282096:ENST00000455098 |
| 11:14843825:A:G | Yes | ENST00000282096:ENST00000455098 |
| 11:14843853:C:T | Yes | ENST00000282096:ENST00000455098 |
| 11:14843922:AT:A | Yes | ENST00000282096:ENST00000455098 |
| 11:14843951:C:A | Yes | ENST00000282096:ENST00000455098 |

TABLE 1-continued

PDE3B Genetic Variants (GRCh38/hg38 human genome assembly)

| Genomic coordinates for the genetic variant, C:P:R:A | Variant classified as pLOF | Transcript |
| --- | --- | --- |
| 11:14843951:C:G | Yes | ENST00000282096:ENST00000455098 |
| 11:14844028:T:G | Yes | ENST00000282096:ENST00000455098 |
| 11:14859111:T:TTC | Yes | ENST00000282096:ENST00000455098 |
| 11:14859176:T:G | Yes | ENST00000282096:ENST00000455098 |
| 11:14859247:GT:G | Yes | ENST00000282096:ENST00000455098 |
| 11:14861232:G:T | Yes | ENST00000282096:ENST00000455098 |
| 11:14861313:C:T | Yes | ENST00000282096:ENST00000455098 |
| 11:14861332:G:A | Yes | ENST00000282096:ENST00000455098 |
| 11:14861367:G:GT | Yes | ENST00000282096:ENST00000455098 |
| 11:14861367:G:T | Yes | ENST00000282096:ENST00000455098 |
| 11:14861368:T:C | Yes | ENST00000282096:ENST00000455098 |
| 11:14867549:T:TG | Yes | ENST00000282096:ENST00000455098 |
| 11:14867573:CA:C | Yes | ENST00000282096:ENST00000455098 |
| 11:14867619:T:A | Yes | ENST00000282096:ENST00000455098 |
| 11:14867658:G:A | Yes | ENST00000282096:ENST00000455098 |
| 11:14867719:GA:G | Yes | ENST00000282096:ENST00000455098 |
| 11:14867756:CAAGT:C | Yes | ENST00000282096:ENST00000455098 |
| 11:14867759:G:T | Yes | ENST00000282096:ENST00000455098 |
| 11:14869487:C:T | Yes | ENST00000282096:ENST00000455098 |
| 11:14869589:C:T | Yes | ENST00000282096:ENST00000455098 |
| 11:14869644:C:CAGAT | Yes | ENST00000282096:ENST00000455098 |
| 11:14869658:T:C | Yes | ENST00000282096:ENST00000455098 |
| 11:14644077:T:G | Yes | ENST00000282096:ENST00000455098 |
| 11:14644077:T:C | Yes | ENST00000282096:ENST00000455098 |
| 11:14644078:G:A | Yes | ENST00000282096:ENST00000455098 |
| 11:14644078:G:C | Yes | ENST00000282096:ENST00000455098 |
| 11:14644095:ACG:A | Yes | ENST00000282096:ENST00000455098 |
| 11:14644141:GC:G | Yes | ENST00000282096:ENST00000455098 |
| 11:14644141:G:GC | Yes | ENST00000282096:ENST00000455098 |
| 11:14644153:T:TTA | Yes | ENST00000282096:ENST00000455098 |
| 11:14644196:C:T | Yes | ENST00000282096:ENST00000455098 |
| 11:14644270:T:TC | Yes | ENST00000282096:ENST00000455098 |
| 11:14644324:C:CGCCCT | Yes | ENST00000282096:ENST00000455098 |
| 11:14644378:G:A | Yes | ENST00000282096:ENST00000455098 |
| 11:14644395:G:A | Yes | ENST00000282096:ENST00000455098 |
| 11:14644396:G:A | Yes | ENST00000282096:ENST00000455098 |
| 11:14644415:G:GT | Yes | ENST00000282096:ENST00000455098 |
| 11:14644434:G:GC | Yes | ENST00000282096:ENST00000455098 |
| 11:14644531:G:A | Yes | ENST00000282096:ENST00000455098 |
| 11:14644534:G:A | Yes | ENST00000282096:ENST00000455098 |
| 11:14644560:AC:A | Yes | ENST00000282096:ENST00000455098 |
| 11:14644582:G:A | Yes | ENST00000282096:ENST00000455098 |
| 11:14644601:T:TG | Yes | ENST00000282096:ENST00000455098 |
| 11:14644602:G:A | Yes | ENST00000282096:ENST00000455098 |
| 11:14644636:CA:C | Yes | ENST00000282096:ENST00000455098 |
| 11:14644795:GC:G | Yes | ENST00000282096:ENST00000455098 |
| 11:14644802:GC:G | Yes | ENST00000282096:ENST00000455098 |
| 11:14644830:T:TG | Yes | ENST00000282096:ENST00000455098 |
| 11:14644904:C:T | Yes | ENST00000282096:ENST00000455098 |
| 11:14644925:GA:G | Yes | ENST00000282096:ENST00000455098 |
| 11:14644930:AG:A | Yes | ENST00000282096:ENST00000455098 |
| 11:14645038:TA:T | Yes | ENST00000282096:ENST00000455098 |
| 11:14645048:G:T | Yes | ENST00000282096:ENST00000455098 |
| 11:14771972:TA:T | Yes | ENST00000282096:ENST00000455098 |
| 11:14771977:C:CTCAA | Yes | ENST00000282096:ENST00000455098 |
| 11:14771984:T:A | Yes | ENST00000282096:ENST00000455098 |
| 11:14771988:GT:G | Yes | ENST00000282096:ENST00000455098 |
| 11:14771988:G:T | Yes | ENST00000282096:ENST00000455098 |
| 11:14786526:AC:A | Yes | ENST00000282096:ENST00000455098 |
| 11:14786554:AT:A | Yes | ENST00000282096 |
| 11:14786634:CT:C | Yes | ENST00000282096 |
| 11:14786686:G:A | Yes | ENST00000282096 |
| 11:14789132:TC:T | Yes | ENST00000282096:ENST00000455098 |
| 11:14789136:C:T | Yes | ENST00000282096:ENST00000455098 |
| 11:14803942:A:T | Yes | ENST00000282096:ENST00000455098 |
| 11:14803943:G:T | Yes | ENST00000282096:ENST00000455098 |
| 11:14803943:G:C | Yes | ENST00000282096:ENST00000455098 |
| 11:14803958:TA:T | Yes | ENST00000282096:ENST00000455098 |
| 11:14803967:CT:C | Yes | ENST00000282096:ENST00000455098 |
| 11:14803982:TA:T | Yes | ENST00000282096:ENST00000455098 |
| 11:14804027:AC:A | Yes | ENST00000282096:ENST00000455098 |
| 11:14804036:GTC:G | Yes | ENST00000282096:ENST00000455098 |
| 11:14818182:G:A | Yes | ENST00000282096:ENST00000455098 |
| 11:14818182:G:C | Yes | ENST00000282096:ENST00000455098 |

TABLE 1-continued

| PDE3B Genetic Variants (GRCh38/hg38 human genome assembly) | | |
|---|---|---|
| Genomic coordinates for the genetic variant, C:P:R:A | Variant classified as pLOF | Transcript |
| 11:14818244:TCTAA:T | Yes | ENST00000282096:ENST00000455098 |
| 11:14818245:C:CT | Yes | ENST00000282096:ENST00000455098 |
| 11:14818254:C:T | Yes | ENST00000282096:ENST00000455098 |
| 11:14818356:C:T | Yes | ENST00000282096:ENST00000455098 |
| 11:14818394:G:T | Yes | ENST00000282096:ENST00000455098 |
| 11:14819134:A:G | Yes | ENST00000282096:ENST00000455098 |
| 11:14819154:GA:G | Yes | ENST00000282096:ENST00000455098 |
| 11:14819165:C:A | Yes | ENST00000282096:ENST00000455098 |
| 11:14819171:CT:C | Yes | ENST00000282096:ENST00000455098 |
| 11:14830697:G:A | Yes | ENST00000282096:ENST00000455098 |
| 11:14830728:C:A | Yes | ENST00000282096:ENST00000455098 |
| 11:14830764:CAG:C | Yes | ENST00000282096:ENST00000455098 |
| 11:14830773:AAGAC:A | Yes | ENST00000282096:ENST00000455098 |
| 11:14830835:C:T | Yes | ENST00000282096:ENST00000455098 |
| 11:14830838:C:T | Yes | ENST00000282096:ENST00000455098 |
| 11:14831639:G:T | Yes | ENST00000282096:ENST00000455098 |
| 11:14831639:G:C | Yes | ENST00000282096:ENST00000455098 |
| 11:14831649:G:T | Yes | ENST00000282096:ENST00000455098 |
| 11:14831659:TG:T | Yes | ENST00000282096:ENST00000455098 |
| 11:14831679:G:T | Yes | ENST00000282096:ENST00000455098 |
| 11:14831689:C:A | Yes | ENST00000282096:ENST00000455098 |
| 11:14831709:A:C | No | ENST00000282096:ENST00000455098 |
| 11:14831725:T:C | No | ENST00000282096:ENST00000455098 |
| 11:14831729:TG:T | Yes | ENST00000282096:ENST00000455098 |
| 11:14831757:TC:T | Yes | ENST00000282096:ENST00000455098 |
| 11:14831764:G:T | No | ENST00000282096:ENST00000455098 |
| 11:14831769:CTCAG:C | Yes | ENST00000282096:ENST00000455098 |
| 11:14831771:C:CA | Yes | ENST00000282096:ENST00000455098 |
| 11:14832719:TA:T | Yes | ENST00000282096:ENST00000455098 |
| 11:14832723:T:C | No | ENST00000282096:ENST00000455098 |
| 11:14832729:A:G | No | ENST00000282096:ENST00000455098 |
| 11:14832738:T:G | No | ENST00000282096:ENST00000455098 |
| 11:14832742:A:T | No | ENST00000282096:ENST00000455098 |
| 11:14832742:AG:A | Yes | ENST00000282096:ENST00000455098 |
| 11:14832743:G:C | No | ENST00000282096:ENST00000455098 |
| 11:14832743:G:A | No | ENST00000282096:ENST00000455098 |
| 11:14832749:G:A | No | ENST00000282096:ENST00000455098 |
| 11:14832774:C:A | No | ENST00000282096:ENST00000455098 |
| 11:14832798:T:G | No | ENST00000282096:ENST00000455098 |
| 11:14832804:C:A | No | ENST00000282096:ENST00000455098 |
| 11:14832805:AT:A | Yes | ENST00000282096:ENST00000455098 |
| 11:14832809:GA:G | Yes | ENST00000282096:ENST00000455098 |
| 11:14832818:TATC:T | Yes | ENST00000282096:ENST00000455098 |
| 11:14832821:C:T | Yes | ENST00000282096:ENST00000455098 |
| 11:14832827:A:AT | Yes | ENST00000282096:ENST00000455098 |
| 11:14832830:C:A | No | ENST00000282096:ENST00000455098 |
| 11:14832831:C:CT | Yes | ENST00000282096:ENST00000455098 |
| 11:14832831:C:A | No | ENST00000282096:ENST00000455098 |
| 11:14832833:TGTAA:T | Yes | ENST00000282096:ENST00000455098 |
| 11:14832835:T:A | Yes | ENST00000282096:ENST00000455098 |
| 11:14834982:A:T | No | ENST00000282096:ENST00000455098 |
| 11:14834984:C:A | No | ENST00000282096:ENST00000455098 |
| 11:14834988:A:G | No | ENST00000282096:ENST00000455098 |
| 11:14834990:C:T | No | ENST00000282096:ENST00000455098 |
| 11:14834991:G:A | No | ENST00000282096:ENST00000455098 |
| 11:14834996:C:T | No | ENST00000282096:ENST00000455098 |
| 11:14835011:C:A | No | ENST00000282096:ENST00000455098 |
| 11:14835014:C:T | No | ENST00000282096:ENST00000455098 |
| 11:14835020:G:A | No | ENST00000282096:ENST00000455098 |
| 11:14835038:C:T | No | ENST00000282096:ENST00000455098 |
| 11:14835096:GT:G | Yes | ENST00000282096:ENST00000455098 |
| 11:14835097:T:C | Yes | ENST00000282096:ENST00000455098 |
| 11:14843825:A:G | Yes | ENST00000282096:ENST00000455098 |
| 11:14843853:C:T | Yes | ENST00000282096:ENST00000455098 |
| 11:14843863:A:G | No | ENST00000282096:ENST00000455098 |
| 11:14843872:C:T | No | ENST00000282096:ENST00000455098 |
| 11:14843901:T:C | No | ENST00000282096:ENST00000455098 |
| 11:14843911:T:C | No | ENST00000282096:ENST00000455098 |
| 11:14843914:C:T | No | ENST00000282096:ENST00000455098 |
| 11:14843920:A:T | No | ENST00000282096:ENST00000455098 |
| 11:14843922:AT:A | Yes | ENST00000282096:ENST00000455098 |
| 11:14843923:T:C | No | ENST00000282096:ENST00000455098 |
| 11:14843923:T:A | No | ENST00000282096:ENST00000455098 |
| 11:14843941:T:A | No | ENST00000282096:ENST00000455098 |

TABLE 1-continued

PDE3B Genetic Variants (GRCh38/hg38 human genome assembly)

| Genomic coordinates for the genetic variant, C:P:R:A | Variant classified as pLOF | Transcript |
|---|---|---|
| 11:14843942:G:A | No | ENST00000282096:ENST00000455098 |
| 11:14843946:C:G | No | ENST00000282096:ENST00000455098 |
| 11:14843951:C:G | Yes | ENST00000282096:ENST00000455098 |
| 11:14843951:C:A | Yes | ENST00000282096:ENST00000455098 |
| 11:14843952:G:A | No | ENST00000282096:ENST00000455098 |
| 11:14843958:G:C | No | ENST00000282096:ENST00000455098 |
| 11:14843968:A:G | No | ENST00000282096:ENST00000455098 |
| 11:14843968:A:C | No | ENST00000282096:ENST00000455098 |
| 11:14843979:C:T | No | ENST00000282096:ENST00000455098 |
| 11:14843985:G:A | No | ENST00000282096:ENST00000455098 |
| 11:14843988:A:G | No | ENST00000282096:ENST00000455098 |
| 11:14843989:G:A | No | ENST00000282096:ENST00000455098 |
| 11:14843992:C:A | No | ENST00000282096:ENST00000455098 |
| 11:14843992:C:T | No | ENST00000282096:ENST00000455098 |
| 11:14843997:G:T | No | ENST00000282096:ENST00000455098 |
| 11:14844006:G:T | No | ENST00000282096:ENST00000455098 |
| 11:14844010:C:T | No | ENST00000282096:ENST00000455098 |
| 11:14844026:G:C | No | ENST00000282096:ENST00000455098 |
| 11:14844028:T:G | Yes | ENST00000282096:ENST00000455098 |
| 11:14859043:G:T | No | ENST00000282096:ENST00000455098 |
| 11:14859053:A:G | No | ENST00000282096:ENST00000455098 |
| 11:14859056:A:G | No | ENST00000282096:ENST00000455098 |
| 11:14859057:T:G | No | ENST00000282096:ENST00000455098 |
| 11:14859062:G:T | No | ENST00000282096:ENST00000455098 |
| 11:14859063:A:T | No | ENST00000282096:ENST00000455098 |
| 11:14859065:C:T | No | ENST00000282096:ENST00000455098 |
| 11:14859074:A:G | No | ENST00000282096:ENST00000455098 |
| 11:14859077:A:G | No | ENST00000282096:ENST00000455098 |
| 11:14859079:C:T | No | ENST00000282096:ENST00000455098 |
| 11:14859080:A:G | No | ENST00000282096:ENST00000455098 |
| 11:14859081:T:A | No | ENST00000282096:ENST00000455098 |
| 11:14859089:C:T | No | ENST00000282096:ENST00000455098 |
| 11:14859099:G:T | No | ENST00000282096:ENST00000455098 |
| 11:14859106:T:C | No | ENST00000282096:ENST00000455098 |
| 11:14859109:C:T | No | ENST00000282096:ENST00000455098 |
| 11:14859109:C:G | No | ENST00000282096:ENST00000455098 |
| 11:14859109:C:A | No | ENST00000282096:ENST00000455098 |
| 11:14859111:T:TTC | Yes | ENST00000282096:ENST00000455098 |
| 11:14859162:G:C | No | ENST00000282096:ENST00000455098 |
| 11:14859163:C:T | No | ENST00000282096:ENST00000455098 |
| 11:14859164:G:T | No | ENST00000282096:ENST00000455098 |
| 11:14859170:G:T | No | ENST00000282096:ENST00000455098 |
| 11:14859170:G:A | No | ENST00000282096:ENST00000455098 |
| 11:14859176:T:G | Yes | ENST00000282096:ENST00000455098 |
| 11:14859176:T:C | No | ENST00000282096:ENST00000455098 |
| 11:14859183:T:G | No | ENST00000282096:ENST00000455098 |
| 11:14859185:A:G | No | ENST00000282096:ENST00000455098 |
| 11:14859200:C:T | No | ENST00000282096:ENST00000455098 |
| 11:14859213:G:C | No | ENST00000282096:ENST00000455098 |
| 11:14859216:T:G | No | ENST00000282096:ENST00000455098 |
| 11:14859220:G:T | No | ENST00000282096:ENST00000455098 |
| 11:14859229:G:A | No | ENST00000282096:ENST00000455098 |
| 11:14859239:A:G | No | ENST00000282096:ENST00000455098 |
| 11:14859247:GT:G | Yes | ENST00000282096:ENST00000455098 |
| 11:14861232:G:T | Yes | ENST00000282096:ENST00000455098 |
| 11:14861254:G:A | No | ENST00000282096:ENST00000455098 |
| 11:14861262:G:A | No | ENST00000282096:ENST00000455098 |
| 11:14861275:G:T | No | ENST00000282096:ENST00000455098 |
| 11:14861277:A:T | No | ENST00000282096:ENST00000455098 |
| 11:14861278:T:C | No | ENST00000282096:ENST00000455098 |
| 11:14861287:C:A | No | ENST00000282096:ENST00000455098 |
| 11:14861293:T:C | No | ENST00000282096:ENST00000455098 |
| 11:14861297:T:G | No | ENST00000282096:ENST00000455098 |
| 11:14861299:G:A | No | ENST00000282096:ENST00000455098 |
| 11:14861301:C:T | No | ENST00000282096:ENST00000455098 |
| 11:14861305:C:A | No | ENST00000282096:ENST00000455098 |
| 11:14861307:A:G | No | ENST00000282096:ENST00000455098 |
| 11:14861313:C:G | No | ENST00000282096:ENST00000455098 |
| 11:14861313:C:T | Yes | ENST00000282096:ENST00000455098 |
| 11:14861332:G:A | Yes | ENST00000282096:ENST00000455098 |
| 11:14861335:C:A | No | ENST00000282096:ENST00000455098 |
| 11:14861338:A:G | No | ENST00000282096:ENST00000455098 |
| 11:14861341:G:A | No | ENST00000282096:ENST00000455098 |
| 11:14861344:T:C | No | ENST00000282096:ENST00000455098 |

TABLE 1-continued

PDE3B Genetic Variants (GRCh38/hg38 human genome assembly)

| Genomic coordinates for the genetic variant, C:P:R:A | Variant classified as pLOF | Transcript |
| --- | --- | --- |
| 11:14861359:A:G | No | ENST00000282096:ENST00000455098 |
| 11:14861365:A:G | No | ENST00000282096:ENST00000455098 |
| 11:14861367:G:T | Yes | ENST00000282096:ENST00000455098 |
| 11:14861367:G:GT | Yes | ENST00000282096:ENST00000455098 |
| 11:14861368:T:C | Yes | ENST00000282096:ENST00000455098 |
| 11:14867507:G:C | No | ENST00000282096:ENST00000455098 |
| 11:14867516:A:C | No | ENST00000282096:ENST00000455098 |
| 11:14867527:G:A | No | ENST00000282096:ENST00000455098 |
| 11:14867534:C:T | No | ENST00000282096:ENST00000455098 |
| 11:14867542:C:G | No | ENST00000282096:ENST00000455098 |
| 11:14867543:C:T | No | ENST00000282096:ENST00000455098 |
| 11:14867548:A:G | No | ENST00000282096:ENST00000455098 |
| 11:14867549:T:TG | Yes | ENST00000282096:ENST00000455098 |
| 11:14867554:C:T | No | ENST00000282096:ENST00000455098 |
| 11:14867555:G:A | No | ENST00000282096:ENST00000455098 |
| 11:14867558:C:G | No | ENST00000282096:ENST00000455098 |
| 11:14867572:G:C | No | ENST00000282096:ENST00000455098 |
| 11:14867573:CA:C | Yes | ENST00000282096:ENST00000455098 |
| 11:14867587:T:A | No | ENST00000282096:ENST00000455098 |
| 11:14867588:C:A | No | ENST00000282096:ENST00000455098 |
| 11:14867593:A:G | No | ENST00000282096:ENST00000455098 |
| 11:14867595:C:G | No | ENST00000282096:ENST00000455098 |
| 11:14867601:C:G | No | ENST00000282096:ENST00000455098 |
| 11:14867605:G:A | No | ENST00000282096:ENST00000455098 |
| 11:14867617:T:C | No | ENST00000282096:ENST00000455098 |
| 11:14867619:T:A | Yes | ENST00000282096:ENST00000455098 |
| 11:14867627:A:T | No | ENST00000282096:ENST00000455098 |
| 11:14867627:A:G | No | ENST00000282096:ENST00000455098 |
| 11:14867658:G:A | Yes | ENST00000282096:ENST00000455098 |
| 11:14867719:GA:G | Yes | ENST00000282096:ENST00000455098 |
| 11:14867756:CAAGT:C | Yes | ENST00000282096:ENST00000455098 |
| 11:14867759:G:T | Yes | ENST00000282096:ENST00000455098 |
| 11:14869484:C:T | No | ENST00000282096:ENST00000455098 |
| 11:14869487:C:T | Yes | ENST00000282096:ENST00000455098 |
| 11:14869535:T:C | No | ENST00000282096:ENST00000455098 |
| 11:14869589:C:T | Yes | ENST00000282096:ENST00000455098 |
| 11:14869644:C:CAGAT | Yes | ENST00000282096:ENST00000455098 |
| 11:14869658:T:C | Yes | ENST00000282096:ENST00000455098 |
| 11:14644687:AG:A | Yes | ENST00000282096:ENST00000455098 |
| 11:14771943:CT:C | Yes | ENST00000282096:ENST00000455098 |
| 11:14771952:TG:T | Yes | ENST00000282096:ENST00000455098 |
| 11:14771980:AT:A | Yes | ENST00000282096:ENST00000455098 |
| 11:14771982:TA:T | Yes | ENST00000282096:ENST00000455098 |
| 11:14789135:AC:A | Yes | ENST00000282096:ENST00000455098 |
| 11:14789145:A:T | Yes | ENST00000282096:ENST00000455098 |
| 11:14789223:C:T | Yes | ENST00000282096:ENST00000455098 |
| 11:14803942:A:G | Yes | ENST00000282096:ENST00000455098 |
| 11:14803971:T:TTA | Yes | ENST00000282096:ENST00000455098 |
| 11:14819139:TG:T | Yes | ENST00000282096:ENST00000455098 |
| 11:14830837:GCAAA:G | Yes | ENST00000282096:ENST00000455098 |
| 11:14834990:CG:C | Yes | ENST00000282096:ENST00000455098 |
| 11:14843888:TC:T | Yes | ENST00000282096:ENST00000455098 |
| 11:14859054:C:A | Yes | ENST00000282096:ENST00000455098 |
| 11:14867653:C:T | Yes | ENST00000282096:ENST00000455098 |

Any one or more (i.e., any combination) of the PDE3B predicted loss-of-function or missense variant nucleic acid molecules can be used within any of the methods described herein to determine whether a subject has an increased risk of developing a liver disease or type 2 diabetes. The combinations of particular variants can form a mask or burden genotype used for statistical analysis of the particular correlation of PDE3B and risk of developing a liver disease or type 2 diabetes.

In any of the embodiments described herein, the liver disease is parenchymal liver disease, liver injury, hepatocellular carcinoma, liver cirrhosis, liver fibrosis, simple steatosis, steatohepatitis, or non-alcoholic steatohepatitis (NASH), liver inflammation, and/or fatty liver disease (such as alcoholic fatty liver disease (AFLD) or nonalcoholic fatty liver disease (NAFLD)). In some embodiments, the liver disease is parenchymal liver disease. In some embodiments, the liver disease is liver injury. In some embodiments, the liver disease is hepatocellular carcinoma. In some embodiments, the liver disease is liver cirrhosis. In some embodiments, the liver disease is liver fibrosis. In some embodiments, the liver disease is simple steatosis. In some embodiments, the liver disease is steatohepatitis. In some embodiments, the liver disease is NASH. In some embodiments, the liver disease is liver inflammation. In some embodiments, the liver disease is a fatty liver disease. In some embodiments, the liver disease is AFLD. In some embodiments, the liver disease is NAFLD.

Symptoms of liver disease include, but are not limited to, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice), pruritus, dark urine color, pale stool color nausea or vomiting, loss of appetite, and tendency to bruise easily. Testing for liver diseases can involve blood tests, imaging of the liver, and biopsy of the liver. An individual is at increased risk of a liver disease if the subject has at least one known risk-factor (e.g., genetic factor such as a disease-causing mutation) placing individuals with that risk factor at a statistically significant greater risk of developing the disease than individuals without the risk factor. Risk factors for liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

Symptoms of diabetes disease include, but are not limited to, increased urination, persistent thirst, weight loss, persistent hunger, blurry vision, numbness in hands and feet, chronic fatigue, dry skin, slow healing sores, increased susceptibility to infections, nausea, vomiting, or stomach pains. A subject is at increased risk of developing a diabetes if the subject has at least one known risk-factor placing individuals with that risk factor at a statistically significant greater risk of developing the disease than individuals without the risk factor. Risk factors for diabetes include, for example, family history, age, presence of prediabetes, excessive body weight, and sedentary lifestyle.

The present disclosure provides methods of treating a subject having a liver disease, or having a risk for developing a liver disease, or who have risk factors for developing a liver disease, or who have a risk of developing complications of a liver disease, the methods comprising administering a PDE3B inhibitor to the subject.

The present disclosure also provides methods of treating a subject having a fatty liver disease, or having a risk for developing a fatty liver disease, or who have risk factors for developing a fatty liver disease, or who have a risk of developing complications of a fatty liver disease, the methods comprising administering a PDE3B inhibitor to the subject.

The present disclosure also provides methods of treating a subject having hepatocellular carcinoma, or having a risk for developing hepatocellular carcinoma, or who have risk factors for developing hepatocellular carcinoma, or who have a risk of developing complications of hepatocellular carcinoma, the methods comprising administering a PDE3B inhibitor to the subject.

The present disclosure also provides methods of treating a subject having liver cirrhosis, or having a risk for developing liver cirrhosis, or who have risk factors for developing liver cirrhosis, or who have a risk of developing complications of liver cirrhosis, the methods comprising administering a PDE3B to the subject.

The present disclosure also provides methods of treating a subject having liver fibrosis, or having a risk for developing liver fibrosis, or who have risk factors for developing liver fibrosis, or who have a risk of developing complications of liver fibrosis, the methods comprising administering a PDE3B inhibitor to the subject.

The present disclosure also provides methods of treating a subject having simple steatosis, steatohepatitis, or NASH, or having a risk for developing simple steatosis, steatohepatitis, or NASH, or who have risk factors for developing simple steatosis, steatohepatitis, or NASH, or who have a risk of developing complications of simple steatosis, steatohepatitis, or NASH, the methods comprising administering a PDE3B inhibitor to the subject.

The present disclosure also provides methods of treating a subject having a liver injury, or having a risk for developing a liver injury, or who have risk factors for developing a liver injury, or who have a risk of developing complications of a liver injury, the methods comprising administering a PDE3B inhibitor to the subject.

The present disclosure also provides methods of treating a subject having type 2 diabetes, or having a risk for developing type 2 diabetes, or who have risk factors for developing type 2 diabetes, or who have a risk of developing complications of type 2 diabetes, the methods comprising administering a PDE3B inhibitor to the subject.

The embodiments described herein can be applied to any subject that has any of the indications described herein, or has a risk for developing any of the indications described herein, or who has risk factors for developing any of the indications described herein, or who has a risk of developing complications of any of the indications described herein.

In some embodiments, the PDE3B inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a PDE3B mRNA. In some embodiments, the antisense RNA, siRNA, or shRNA hybridizes to a sequence within a PDE3B genomic nucleic acid molecule or mRNA molecule and decreases expression of the PDE3B polypeptide in a cell in the subject. In some embodiments, the PDE3B inhibitor comprises an antisense RNA that hybridizes to a PDE3B genomic nucleic acid molecule or mRNA molecule and decreases expression of the PDE3B polypeptide in a cell in the subject. In some embodiments, the PDE3B inhibitor comprises an siRNA that hybridizes to a PDE3B genomic nucleic acid molecule or mRNA molecule and decreases expression of the PDE3B polypeptide in a cell in the subject. In some embodiments, the PDE3B inhibitor comprises an shRNA that hybridizes to a PDE3B genomic nucleic acid molecule or mRNA molecule and decreases expression of the PDE3B polypeptide in a cell in the subject.

In some embodiments, the antisense nucleic acid molecules comprise or consist of any of the nucleotide sequences represented by SEQ ID NOs: 35-864. In some embodiments, the siRNA molecules comprise or consist of any of the nucleotide sequences (sense and antisense strands) represented by SEQ ID NOs: 865-3210 (e.g., the sense strand is, for example, SEQ ID NO:865 and the corresponding antisense strand is SEQ ID NO:866; the sense strand is, for example, SEQ ID NO:867 and the corresponding antisense strand is SEQ ID NO:868; the sense strand is, for example, SEQ ID NO:3209 and the corresponding antisense strand is SEQ ID NO:3210; etc.).

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3XFLAG, 6XHis or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ON H$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N3, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/ i2FN/mN/i2FN/mN/i2FN/mN/i2FN/*mN*/32FN/
Antisense: /52FN/*/i2FN/*mN/i2FN/mN/i2FN/mN/i2FN/ mN/i2FN/mN/i2FN/mN/i2FN/mN/i2FN/mN/i2FN/ mN*N*N wherein: "N" is the base; "2F" is a 2'-F modification; "m" is a 2'-O-methyl modification, "I" is an internal base; and "*" is a phosphorothioate backbone linkage. The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the PDE3B inhibitor is described in, for example, PCT Publication No. WO 2002/070469, U.S. Patent Application Publication No. 2020/0247783. In some embodiments, the PDE3B inhibitor is chosen from OPC3911, IBMX, 3-isobutyl-1-methylxanthine, dihydropyridazinone, amrinone, enoximone, cilostamide, milrinone, cilostazol, and levosimendan. In some embodiments, the PDE3B inhibitor is OPC3911. In some embodiments, the PDE3B inhibitor is IBMX. In some embodiments, the PDE3B inhibitor is 3-isobutyl-1-methylxanthine. In some embodiments, the PDE3B inhibitor is dihydropyridazinone. In some embodiments, the PDE3B inhibitor is amrinone. In some embodiments, the PDE3B inhibitor is enoximone. In some embodiments, the PDE3B inhibitor is cilostamide. In some embodiments, the PDE3B inhibitor is milrinone. In some embodiments, the PDE3B inhibitor is cilostazol. In some embodiments, the PDE3B inhibitor is levosimendan.

In some embodiments, the PDE3B inhibitor comprises a nuclease agent that induces one or more nicks or double-strand breaks at a recognition sequence(s) or a DNA-binding protein that binds to a recognition sequence within a PDE3B genomic nucleic acid molecule. The recognition sequence can be located within a coding region of the PDE3B gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the PDE3B gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a PDE3B genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of PDE3B nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a PDE3B genomic nucleic acid molecule or it can be a nickase that creates a single-strand break in a PDE3B genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of PDE3B genomic nucleic acid molecules can be generated by contacting a cell with a Cas protein and one or more gRNAs that hybridize to one or more gRNA recognition sequences within a target genomic locus in the PDE3B genomic nucleic acid molecule. For example, a gRNA recognition sequence can be located within a region of SEQ ID NO:1. The gRNA recognition sequence can include or be proximate to the start codon of a PDE3B genomic nucleic acid molecule or the stop codon of a PDE3B genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a PDE3B genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from S. *pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a PDE3B genomic nucleic acid molecule. An exemplary gRNA is a gRNA effective to direct a Cas enzyme to bind to or cleave a PDE3B genomic nucleic acid molecule, wherein the gRNA comprises a DNA-targeting segment that hybridizes to a gRNA recognition sequence within the PDE3B genomic nucleic acid molecule. Exemplary gRNAs comprise a DNA-targeting segment that hybridizes to a gRNA recognition sequence present within a PDE3B genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human PDE3B reference gene are set forth in Table 2 as SEQ ID NOs:26-34.

TABLE 2

| Guide RNA Recognition Sequences Near PDE3B Variation(s) | | |
|---|---|---|
| Strand | gRNA Recognition Sequence | SEQ ID NO: |
| + | CTGTTGAACAGTCTTCAAGG | 26 |
| + | TGATCTTTTAGTGCTAAATG | 27 |
| - | TCGGCGGCACTGGACAGTCG | 28 |
| + | TTCCTCACCCGGACCAAGCG | 29 |
| - | GATCTCTGCAAGATAACGCT | 30 |
| + | CTGCCGGGCGCGCCTCTCGC | 31 |
| + | TGCCGGGCGCGCCTCTCGCT | 32 |
| - | GGGAGCAGCGCCGCGGCTGC | 33 |
| - | GCCGGGTCCCCGCTTGGTCC | 34 |

The Cas protein and the gRNA form a complex, and the Cas protein cleaves the target PDE3B genomic nucleic acid molecule. The Cas protein can cleave the nucleic acid molecule at a site within or outside of the nucleic acid sequence present in the target PDE3B genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the PDE3B genomic nucleic acid molecule to which a DNA-targeting segment of a gRNA will bind.

Such methods can result, for example, in a PDE3B genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the PDE3B genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment further comprise detecting the presence or absence of a PDE3B predicted loss-of-function or missense variant nucleic acid molecule encoding a human PDE3B polypeptide in a biological sample from the subject. As used throughout the present disclosure, a "PDE3B predicted loss-of-function variant nucleic acid molecule" is any PDE3B nucleic acid molecule (such as, for example, genomic nucleic acid molecule, mRNA molecule, or cDNA molecule) encoding a PDE3B polypeptide having a partial loss-of-function, a complete loss-of-function, a predicted partial loss-of-function, or a predicted complete loss-of-function.

The present disclosure also provides methods of treating a subject with a therapeutic agent that treats or inhibits a liver disease or type 2 diabetes, wherein the subject is suffering from a liver disease or type 2 diabetes. In some embodiments, the methods comprise determining whether the subject has a PDE3B predicted loss-of-function or missense variant nucleic acid molecule encoding a human PDE3B polypeptide by obtaining or having obtained a biological sample from the subject, and performing or having performed a sequence analysis on the biological sample to determine if the subject has a genotype comprising the PDE3B predicted loss-of-function or missense variant nucleic acid molecule. When the subject is PDE3B reference, the therapeutic agent that treats or inhibits a liver disease or type 2 diabetes is administered or continued to be administered to the subject in an amount that is greater than a standard dosage amount, and a PDE3B inhibitor is administered to the subject. When the subject is heterozygous for a PDE3B predicted loss-of-function or missense variant, the therapeutic agent that treats or inhibits a liver disease or type 2 diabetes is administered or continued to be administered to the subject in an amount that is the same as or less than a standard dosage amount, and a PDE3B inhibitor is administered to the subject. The presence of a genotype having the PDE3B predicted loss-of-function or missense variant nucleic acid molecule encoding the human PDE3B polypeptide indicates the subject has a decreased risk of developing a liver disease or type 2 diabetes. In some embodiments, the subject is PDE3B reference. In some embodiments, the subject is heterozygous for a PDE3B predicted loss-of-function or missense variant nucleic acid molecule.

For subjects that are genotyped or determined to be either PDE3B reference or heterozygous for a PDE3B predicted loss-of-function or missense variant, such subjects can be treated with a PDE3B inhibitor, as described herein.

Detecting the presence or absence of a PDE3B predicted loss-of-function or missense variant nucleic acid molecule in a biological sample from a subject and/or determining whether a subject has a PDE3B predicted loss-of-function or missense variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is PDE3B reference, the subject is also administered a therapeutic agent that treats or inhibits liver disease or type 2 diabetes in an amount that is greater than a standard dosage amount. In some embodiments, when the subject is heterozygous for a PDE3B predicted loss-of-function or missense variant, the subject is also administered a therapeutic agent that treats or inhibits liver disease or type 2 diabetes in a dosage amount that is the same as or less than a standard dosage amount.

In some embodiments, the treatment methods further comprise detecting the presence or absence of a PDE3B predicted loss-of-function polypeptide in a biological sample from the subject. In some embodiments, when the subject does not have a PDE3B predicted loss-of-function polypeptide, the subject is also administered a therapeutic agent that treats or inhibits liver disease or type 2 diabetes in an amount that is greater than a standard dosage amount. In some embodiments, when the subject has a PDE3B predicted loss-of-function polypeptide, the subject is also administered a therapeutic agent that treats or inhibits liver disease or type 2 diabetes in a dosage amount that is the same as or less than a standard dosage amount.

The present disclosure also provides methods of treating a subject with a therapeutic agent that treats or inhibits liver disease or type 2 diabetes, wherein the subject is suffering from liver disease or type 2 diabetes. In some embodiments, the method comprises determining whether the subject has a PDE3B predicted loss-of-function polypeptide by obtaining or having obtained a biological sample from the subject, and performing or having performed an assay on the biological sample to determine if the subject has a PDE3B predicted loss-of-function polypeptide. When the subject does not have a PDE3B predicted loss-of-function polypeptide, the therapeutic agent that treats or inhibits liver disease or type 2 diabetes is administered or continued to be administered to the subject in an amount that is greater than a standard dosage amount, and a PDE3B inhibitor is administered to the subject. When the subject has a PDE3B predicted loss-of-function polypeptide, the therapeutic agent that treats or inhibits liver disease or type 2 diabetes is administered or continued to be administered to the subject in an amount that is the same as or less than a standard dosage amount, and a PDE3B inhibitor is administered to the subject. The presence of a PDE3B predicted loss-of-function polypeptide indicates the subject has a decreased risk of developing liver disease or type 2 diabetes. In some embodiments, the subject has a PDE3B predicted loss-of-function polypeptide. In some embodiments, the subject does not have a PDE3B predicted loss-of-function polypeptide.

Detecting the presence or absence of a PDE3B predicted loss-of-function polypeptide in a biological sample from a subject and/or determining whether a subject has a PDE3B predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit liver disease include, but are not limited to: disulfiram, naltrexone, acamprosate, prednisone, azathioprine, penicillamine, trientine, deferoxamine, ciprofloxacin, norofloxacin, ceftriaxone, ofloxacin, amoxicillin-clavulanate, phytonadione, bumetanide, furosemide, hydrochlorothiazide, chlorothiazide, amiloride, triamterene, spironolactone, octreotide, atenolol, metoprolol, nadolol, propranolol, timolol, and carvedilol, or any combination thereof. In some embodiments, the therapeutic agent that treats or inhibits liver disease is disulfiram. In some embodiments, the therapeutic agent that treats or inhibits liver disease is naltrexone. In some embodiments, the therapeutic agent that treats or inhibits liver disease is acamprosate. In some embodiments, the therapeutic agent that treats or inhibits liver disease is prednisone. In some embodiments, the therapeutic agent that treats or inhibits liver disease is azathioprine. In some embodiments, the therapeutic agent that treats or inhibits liver disease is penicillamine. In some embodiments, the therapeutic agent that treats or inhibits liver disease is trientine. In some embodiments, the therapeutic agent that treats or inhibits liver disease is deferoxamine. In some embodiments, the therapeutic agent that treats or inhibits liver disease is ciprofloxacin. In some embodiments, the therapeutic agent that treats or inhibits liver disease is norofloxacin. In some embodiments, the therapeutic agent that treats or inhibits liver disease is ceftriaxone. In some embodiments, the therapeutic agent that treats or inhibits liver disease is ofloxacin. In some embodiments, the therapeutic agent that treats or inhibits liver disease is amoxicillin-clavulanate. In some embodiments, the therapeutic agent that treats or inhibits liver disease is phytonadione. In some embodiments, the therapeutic agent that treats or inhibits liver disease is bumetanide. In some embodiments, the therapeutic agent that treats or inhibits liver disease is furosemide. In some embodiments, the therapeutic agent that treats or inhibits liver disease is hydrochlorothiazide. In some embodiments, the therapeutic agent that treats or inhibits liver disease is chlorothiazide. In some embodiments, the therapeutic agent that treats or inhibits liver disease is amiloride. In some embodiments, the therapeutic agent that treats or inhibits liver disease is triamterene. In some embodiments, the therapeutic agent that treats or inhibits liver disease is spironolactone. In some embodiments, the therapeutic agent that treats or inhibits liver disease is octreotide. In some embodiments, the therapeutic agent that treats or inhibits liver disease is atenolol. In some embodiments, the therapeutic agent that treats or inhibits liver disease is metoprolol. In some embodiments, the therapeutic agent that treats or inhibits liver disease is nadolol. In some embodiments, the therapeutic agent that treats or inhibits liver disease is propranolol. In some embodiments, the therapeutic agent that treats or inhibits liver disease is timolol. In some embodiments, the therapeutic agent that treats or inhibits liver disease is carvedilol.

Examples of therapeutic agents that treat or inhibit type 2 diabetes include, but are not limited to: metformin, insulin, sulfonylureas (such as glyburide, glipizide, and glimepiride), meglitinides (such as repaglinide and nateglinide), thiazolidinediones (such as rosiglitazone and pioglitazone), DPP-4 inhibitors (such as sitagliptin, saxagliptin, and linagliptin), GLP-1 receptor agonists (such as exenatide, liraglutide, and semagiutide), and SGLT2 inhibitors (such as canagliflozin, dapagliflozin, and empagliflozin). In some embodiments, the therapeutic agent is metformin, insulin, glyburide, glipizide, glimepiride, repaglinide, nateglinide, rosiglitazone, pioglitazone, sitagliptin, saxagliptin, linagliptin, exenatide, liraglutide, semaglutide, canagliflozin, dapagliflozin, or empagliflozin. In some embodiments, the therapeutic agent is metformin. In some embodiments, the therapeutic agent is insulin. In some embodiments, the therapeutic agent is glyburide. In some embodiments, the therapeutic agent is glipizide. In some embodiments, the therapeutic agent is glimepiride. In some embodiments, the therapeutic agent is repaglinide. In some embodiments, the therapeutic agent is nateglinide. In some embodiments, the therapeutic agent is rosiglitazone. In some embodiments, the therapeutic agent is pioglitazone. In some embodiments, the therapeutic agent is sitagliptin. In some embodiments, the therapeutic agent is saxagliptin. In some embodiments, the therapeutic agent is linagliptin. In some embodiments, the therapeutic agent is exenatide. In some embodiments, the therapeutic agent is liraglutide. In some embodiments, the therapeutic agent is semaglutide. In some embodiments, the therapeutic agent is canagliflozin. In some embodiments, the therapeutic agent is dapagliflozin. In some embodiments, the therapeutic agent is empagliflozin.

Examples of therapeutic agents that treat or inhibit liver cirrhosis include, but are not limited to: disulfiram, naltrexone, acamprosate, corticosteroids (such as prednisone and azathioprine), antiviral agents (such as interferons, protease inhibitors, and reverse transcriptase inhibitors), chelating agents (such as penicillamine, trientine, and deferoxamine), diuretics (such as bumetanide, furosemide, hydrochlorothiazide, chlorothiazide, amiloride, triamterene, and spironolactone), and beta-blockers (such as atenolol, metoprolol, nadolol, propranolol, timolol, and carvedilol). In some embodiments, the therapeutic agent that treats or inhibits liver cirrhosis is disulfiram. In some embodiments, the therapeutic agent that treats or inhibits liver cirrhosis is naltrexone. In some embodiments, the therapeutic agent that treats or inhibits liver cirrhosis is acamprosate. In some embodiments, the therapeutic agent that treats or inhibits liver cirrhosis is a corticosteroid (such as prednisone and azathioprine). In some embodiments, the therapeutic agent that treats or inhibits liver cirrhosis is an antiviral agent (such as interferons, protease inhibitors, and reverse transcriptase inhibitors). In some embodiments, the therapeutic agent that treats or inhibits liver cirrhosis is a chelating agent (such as penicillamine, trientine, and deferoxamine). In some embodiments, the therapeutic agent that treats or inhibits liver cirrhosis is a diuretic (such as bumetanide, furosemide, hydrochlorothiazide, chlorothiazide, amiloride, triamterene, and spironolactone). In some embodiments, the therapeutic agent that treats or inhibits liver cirrhosis is a beta-blocker (such as atenolol, metoprolol, nadolol, propranolol, timolol, and carvedilol).

Additional examples of liver disease therapeutic agents (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; anti-oxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA); ACE inhibitors/ARBs, oligofructose, and Incretin analogs. In some embodiments, the therapeutic agent for treating nonalcoholic fatty liver disease is a weight loss inducing agent (such as orlistat or sibutramine). In some embodiments, the therapeutic agent for treating nonalcoholic fatty liver disease is an insulin sensitizing agent (such as thiazolidinediones (TZDs), metformin, and meglitinides). In some embodiments, the therapeutic agent for treating nonalcoholic fatty liver disease is a lipid lowering agent (such as statins, fibrates, and omega-3 fatty acids). In some embodiments, the therapeutic agent for treating nonalcoholic fatty liver disease is an antioxidant such as vitamin E, betaine, N-Acetyl-cysteine, lecithin, silymarin, and beta-carotene. In some embodiments, the therapeutic agent for treating nonalcoholic fatty liver disease is an anti TNF agent (such as pentoxifylline). In some embodiments, the therapeutic agent for treating nonalcoholic fatty liver disease is a probiotic (such as VSL #3). In some embodiments, the therapeutic agent for treating nonalcoholic fatty liver disease is a cytoprotective agent (such as ursodeoxycholic acid (UDCA)). In some embodiments, the therapeutic agent for treating nonalcoholic fatty liver disease is an ACE inhibitors/ARBs. In some embodiments, the therapeutic agent for treating nonalcoholic fatty liver disease is oligofructose. In some embodiments, the therapeutic agent for treating nonalcoholic fatty liver disease is an Incretin analog.

Additional examples of liver disease therapeutic agents (e.g., for use in NASH) include, but are not limited to, OCALIVA® (obeticholic acid), Selonsertib, Elafibranor, Cenicriviroc, GR_MD_02, MGL_3196, IMM_124E, arachidyl amido cholanoic acid (ARAMCHOL™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

In addition, a subject may be treated with bariatric surgery and/or dietary intervention.

Additional examples of liver disease therapeutic agents (e.g., for use in chronic hepatitis C treatment) include, but are not limited to, ribavirin, paritaprevir, OLYSIO™ (simeprevir), grazoprevir, ledipasvir, ombitasvir, elbasvir, DAKLINZA® (daclatasvir), dasabuvir, ritonavir, sofosbuvir, velpatasvir, voxilaprevir, glecaprevir, pibrentasvir, peginterferon alfa-2a, peginterferon alfa-2b, and interferon alfa-2b.

In some embodiments, the dose of the therapeutic agents that treat or inhibit liver diseases or type 2 diabetes can be decreased by about 10%, by about 20%, by about 30%, by about 40%, by about 50%, by about 60%, by about 70%, by about 80%, or by about 90% for subjects that are heterozygous for a PDE3B predicted loss-of-function or missense variant (i.e., a less than the standard dosage amount) compared to subjects that are PDE3B reference (who may receive an amount that is greater than a standard dosage amount). In some embodiments, the dose of the therapeutic agents that treat or inhibit liver diseases or type 2 diabetes can be decreased by about 10%, by about 20%, by about 30%, by about 40%, or by about 50%. In addition, the subjects that are heterozygous for a PDE3B predicted loss-of-function or missense variant can be administered less frequently compared to subjects that are PDE3B reference.

In some embodiments, the dose of the therapeutic agents that treat or inhibit a liver disease or type 2 diabetes can be decreased by about 10%, by about 20%, by about 30%, by about 40%, by about 50%, for subjects that are homozygous for a PDE3B predicted loss-of-function or missense variant nucleic acid molecule compared to subjects that are heterozygous for a PDE3B predicted loss-of-function or missense variant nucleic acid molecule. In some embodiments, the dose of the therapeutic agents that treat or inhibit a liver disease or type 2 diabetes can be decreased by about 10%, by about 20%, by about 30%, by about 40%, by about 50%. In addition, the dose of therapeutic agents that treat or inhibit liver disease or type 2 diabetes in subjects that are homozygous for a PDE3B predicted loss-of-function or missense variant nucleic acid molecule can be administered less frequently compared to subjects that are heterozygous for a PDE3B predicted loss-of-function or missense variant nucleic acid molecule.

Administration of the therapeutic agents that treat or inhibit liver diseases or type 2 diabetes and/or PDE3B inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more. Administration of the therapeutic agents that treat or inhibit liver diseases or type 2 diabetes and/or PDE3B inhibitors can occur by any suitable route including, but not limited to, parenteral, intravenous, oral, subcutaneous, intraarterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in liver diseases or type 2 diabetes, a decrease/reduction in the severity of liver diseases or type 2 diabetes (such as, for example, a reduction or inhibition of development or liver diseases), a decrease/reduction in symptoms and liver disease-related effects or type 2 diabetes-related effects, delaying the onset of symptoms and liver disease-related effects or type 2 diabetes-related effects, reducing the severity of symptoms of liver disease-related effects or type 2 diabetes-related effects, reducing the number of symptoms and liver disease-related effects or type 2 diabetes-related effects, reducing the latency of symptoms and liver disease-related effects or type 2 diabetes-related effects, an amelioration of symptoms and liver disease-related effects or type 2 diabetes-related effects, reducing secondary symptoms, reducing secondary infections, preventing relapse to liver diseases or type 2 diabetes, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of liver diseases or type 2 diabetes development/progression (such as, for example, a complete or partial avoidance/inhibition or a delay), and an increased survival time of the affected host animal, following administration of a therapeutic protocol. Treatment of liver diseases or type 2 diabetes encompasses the treatment of subjects already diagnosed as having any form of liver diseases or type 2 diabetes at any clinical stage or manifestation, the delay of the onset or evolution or aggravation or deterioration of the symptoms or signs of liver diseases or type 2 diabetes, and/or preventing and/or reducing the severity of liver diseases or type 2 diabetes.

The present disclosure also provides methods of identifying a subject having an increased risk of developing a liver disease or type 2 diabetes. In some embodiments, the method comprises determining or having determined in a biological sample obtained from the subject the presence or absence of a PDE3B predicted loss-of-function or missense variant nucleic acid molecule (such as a genomic nucleic acid molecule, mRNA molecule, and/or cDNA molecule) encoding a human PDE3B polypeptide. When the subject lacks a PDE3B predicted loss-of-function or missense variant nucleic acid molecule (i.e., the subject is genotypically categorized as a PDE3B reference), then the subject has an increased risk of developing a liver disease or type 2 diabetes. When the subject has a PDE3B predicted loss-of-function or missense variant nucleic acid molecule (i.e., the subject is heterozygous for a PDE3B predicted loss-of-function or missense variant or homozygous for a PDE3B predicted loss-of-function or missense variant), then the subject has a decreased risk of developing a liver disease or type 2 diabetes. In some embodiments, liver expression quantitative trait loci (eQTL) can be analyzed.

Having a single copy of a PDE3B predicted loss-of-function or missense variant nucleic acid molecule is more protective of a subject from developing a liver disease or type 2 diabetes than having no copies of a PDE3B predicted loss-of-function or missense variant nucleic acid molecule. Without intending to be limited to any particular theory or mechanism of action, it is believed that a single copy of a PDE3B predicted loss-of-function or missense variant nucleic acid molecule (i.e., heterozygous for a PDE3B predicted loss-of-function or missense variant) is protective of a subject from developing a liver disease or type 2 diabetes, and it is also believed that having two copies of a PDE3B predicted loss-of-function or missense variant nucleic acid molecule (i.e., homozygous for a PDE3B predicted loss-of-function or missense variant) may be more protective of a subject from developing a liver disease or type 2 diabetes, relative to a subject with a single copy. Thus, in some embodiments, a single copy of a PDE3B predicted loss-of-function or missense variant nucleic acid molecule may not be completely protective, but instead, may be partially or incompletely protective of a subject from developing a liver disease or type 2 diabetes. While not desiring to be bound by any particular theory, there may be additional factors or molecules involved in the development of liver diseases or type 2 diabetes that are still present in a subject having a single copy of a PDE3B predicted loss-of-function or missense variant nucleic acid molecule, thus resulting in less than complete protection from the development of liver diseases or type 2 diabetes.

Determining whether a subject has a PDE3B predicted loss-of-function or missense variant nucleic acid molecule in a biological sample from a subject and/or determining whether a subject has a PDE3B predicted loss-of-function or missense variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing a liver disease or type 2 diabetes, the subject is further treated with a therapeutic agent that treats or inhibits liver diseases or type 2 diabetes, and/or a PDE3B inhibitor, as described herein. For example, when the subject is PDE3B reference, and therefore has an increased risk of developing a liver disease or type 2 diabetes, the subject is administered a PDE3B inhibitor. In some embodiments, such a subject is also administered a therapeutic agent that treats or inhibits liver diseases or type 2 diabetes. In some embodiments, when the subject is heterozygous for a PDE3B predicted loss-of-function or missense variant nucleic acid molecule, the subject is administered the therapeutic agent that treats or inhibits liver diseases or type 2 diabetes in a dosage amount that is the same as or less than a standard dosage amount, and is also administered a PDE3B inhibitor. In some embodiments, such a subject is also administered a therapeutic agent that treats or inhibits liver diseases or type 2 diabetes. In some embodiments, when the subject is homozygous for a PDE3B predicted loss-of-function or missense variant nucleic acid molecule, the subject is administered the therapeutic agent that treats or inhibits liver diseases or type 2 diabetes in a dosage amount that is the same as or less than a standard dosage amount. In some embodiments, the subject is PDE3B reference. In some embodiments, the subject is heterozygous for a PDE3B predicted loss-of-function or missense variant nucleic acid molecule. In some embodiments, the subject is homozygous for a PDE3B predicted loss-of-function or missense variant nucleic acid molecule.

In some embodiments, any of the methods described herein can further comprise determining the subject's aggregate burden of having a PDE3B predicted loss-of-function or missense variant genomic nucleic acid molecule, mRNA molecule, or cDNA molecule produced from an mRNA molecule, and/or a PDE3B predicted loss-of-function variant polypeptide associated with a decreased risk of developing liver disease or type 2 diabetes. The aggregate burden is the sum of all variants in the PDE3B gene (including any genetic variants, regardless of their genomic annotation, in proximity to the PDE3B gene—up to 10 Mb around the gene), which can be carried out in an association analysis with liver disease or type 2 diabetes. In some embodiments, the subject is homozygous for one or more PDE3B predicted loss-of-function or missense variant nucleic acid molecules associated with a decreased risk of developing liver disease or type 2 diabetes. In some embodiments, the subject is heterozygous for one or more PDE3B predicted loss-of-function or missense variant nucleic acid molecules associated with a decreased risk of developing liver disease or type 2 diabetes. The result of the association analysis suggests that PDE3B predicted loss-of-function and missense variants are associated with decreased risk of developing liver disease or type 2 diabetes. When the subject has a lower aggregate burden, the subject is at a higher risk of developing a liver disease or type 2 diabetes and the subject is administered or continued to be administered the therapeutic agent that treats or inhibits liver disease or type 2 diabetes in an amount that is greater than a standard dosage amount.

When the subject has a greater aggregate burden, the subject is at a lower risk of developing a liver disease or type 2 diabetes and the subject is administered or continued to be administered the therapeutic agent that treats or inhibits liver disease or type 2 diabetes in an amount that is the same as or less than the standard dosage amount. The greater the aggregate burden, the lower the risk of developing liver disease or type 2 diabetes.

In some embodiments, the subject's aggregate burden of having any one or more PDE3B predicted loss-of-function or missense variant nucleic acid molecules represents a weighted sum of a plurality of any of the PDE3B predicted loss-of-function or missense variant nucleic acid molecules. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the PDE3B gene where the genetic burden is the number of alleles multiplied by the association estimate with liver disease or related outcome for each allele (e.g., a weighted polygenic burden score). This can include any genetic variants, regardless of their genomic annotation, in proximity to the PDE3B gene (up to 10 Mb around the gene) that show a non-zero association with liver-related traits in a genetic association analysis. In some embodiments, when the subject has an aggregate burden above a desired threshold score, the subject has a decreased risk of developing a liver disease or type 2 diabetes. In some embodiments, when the subject has an aggregate burden below a desired threshold score, the subject has an increased risk of developing a liver disease or type 2 diabetes.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprises the highest weighted aggregate burdens, including, but not limited to the top 10%, top 20%, top 30%, top 40%, or top 50% of aggregate burdens from a subject population. In some embodiments, the genetic variants comprise the genetic variants having association with a liver disease or type 2 diabetes in the top 10%, top 20%, top 30%, top 40%, or top 50% of p-value range for the association. In some embodiments, each of the identified genetic variants comprise the genetic variants having association with a liver disease or type 2 diabetes with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with a liver disease or type 2 diabetes with p-value of less than $5\times10^{-8}$. In some embodiments, the identified genetic variants comprise genetic variants having association with a liver disease or type 2 diabetes in high-risk subjects as compared to the rest of the reference population with odds ratio (OR) about 1.001 or greater, about 1.01 or greater, about 1.1 or greater, about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.001 to about 1.01, from about 1.01 to about 1.1, from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having aggregate burdens in the bottom decile, quintile, or tertile in a reference population. The threshold of the aggregate burden is determined on the basis of the nature of the intended practical application and the risk difference that would be considered meaningful for that practical application.

In some embodiments, when a subject is identified as having an increased risk of developing liver disease or type 2 diabetes, the subject is further treated with a therapeutic agent that treats or inhibits liver disease or type 2 diabetes, and/or a PDE3B inhibitor, as described herein. For example, when the subject is PDE3B reference, and therefore has an increased risk of developing liver disease or type 2 diabetes, the subject is administered a PDE3B inhibitor. In some embodiments, such a subject is also administered a therapeutic agent that treats or inhibits liver disease or type 2 diabetes. In some embodiments, when the subject is heterozygous for a PDE3B predicted loss-of-function or missense variant, the subject is administered the therapeutic agent that treats or inhibits liver disease or type 2 diabetes in a dosage amount that is the same as or less than a standard dosage amount, and is also administered a PDE3B inhibitor. In some embodiments, the subject is PDE3B reference. In some embodiments, the subject is heterozygous for a PDE3B predicted loss-of-function or missense variant nucleic acid molecule. Furthermore, when the subject has a lower aggregate burden for having a PDE3B predicted loss-of-function or missense variant nucleic acid molecule, and therefore has an increased risk of developing liver disease or type 2 diabetes, the subject is administered a therapeutic agent that treats or inhibits liver disease or type 2 diabetes in an amount that is greater than a standard dosage amount. In some embodiments, when the subject has a lower aggregate burden for having a PDE3B predicted loss-of-function or missense variant nucleic acid molecule, the subject is administered the therapeutic agent that treats or inhibits liver disease or type 2 diabetes in a dosage amount that is the same as or less than the standard dosage amount administered to a subject who has a greater aggregate burden for having a PDE3B predicted loss-of-function or missense variant nucleic acid molecule.

The present disclosure also provides methods of detecting the presence or absence of a PDE3B predicted loss-of-function or missense variant genomic nucleic acid molecule in a biological sample from a subject, and/or a PDE3B predicted loss-of-function or missense variant mRNA molecule in a biological sample from a subject, and/or a PDE3B predicted loss-of-function or missense variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the PDE3B variant genomic nucleic acid molecule, PDE3B variant mRNA molecule, and PDE3B variant cDNA molecule are only exemplary sequences. Other sequences for the PDE3B variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any PDE3B variant nucleic acid molecule, preliminary processing designed to isolate or enrich the biological sample for the genomic DNA can be employed. A variety of techniques may be used for this purpose. When detecting the level of any PDE3B variant mRNA molecule, different techniques can be used enrich the biological sample with mRNA molecules. Various methods to detect the presence or level of an mRNA molecule or the presence of a particular variant genomic DNA locus can be used.

In some embodiments, detecting a PDE3B predicted loss-of-function or missense variant nucleic acid molecule in a subject comprises performing a sequence analysis on a biological sample obtained from the subject to determine whether a PDE3B genomic nucleic acid molecule in the biological sample, and/or a PDE3B mRNA molecule in the biological sample, and/or a PDE3B cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a PDE3B predicted loss-of-function or missense variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a PDE3B genomic nucleic acid molecule or mRNA molecule, and if mRNA, optionally reverse transcribing the mRNA into cDNA. Such assays can comprise, for example determining the identity of these positions of the particular PDE3B nucleic acid molecule. In some embodiments, the method is an in vitro method.

In some embodiments, the determining step, detecting step, or sequence analysis comprises sequencing at least a portion of the nucleotide sequence of the PDE3B genomic nucleic acid molecule, the PDE3B mRNA molecule, or the PDE3B cDNA molecule in the biological sample, wherein the sequenced portion comprises one or more variations that cause a loss-of-function (partial or complete) or are predicted to cause a loss-of-function (partial or complete).

In some embodiments, the assay comprises sequencing the entire nucleic acid molecule. In some embodiments, only a PDE3B genomic nucleic acid molecule is analyzed. In some embodiments, only a PDE3B mRNA is analyzed. In some embodiments, only a PDE3B cDNA obtained from PDE3B mRNA is analyzed.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a PDE3B variant genomic sequence, variant mRNA sequence, or variant cDNA sequence and not the corresponding PDE3B reference sequence under stringent conditions, and determining whether hybridization has occurred.

In some embodiments, the determining step, detecting step, or sequence analysis comprises: a) amplifying at least a portion of the nucleic acid molecule that encodes the PDE3B polypeptide; b) labeling the amplified nucleic acid molecule with a detectable label; c) contacting the labeled nucleic acid molecule with a support comprising an alteration-specific probe; and d) detecting the detectable label.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a PDE3B variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6×sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to PDE3B variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to PDE3B variant genomic nucleic acid molecules, PDE3B variant mRNA molecules, and/or PDE3B variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the PDE3B variant genomic nucleic acid molecules, PDE3B variant mRNA molecules, and/or PDE3B variant cDNA molecules disclosed herein. The primers described herein can be used to amplify PDE3B variant genomic nucleic acid molecules, PDE3B variant mRNA molecules, or PDE3B variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a PDE3B reference genomic nucleic acid molecule, a PDE3B reference mRNA molecule, and/or a PDE3B reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a PDE3B reference genomic nucleic acid molecule is set forth in SEQ ID NO:1 (ENSG00000152270.9 encompassing chr11:14,643,804-14,872,044 in the GRCh38/hg38 human genome assembly).

The nucleotide sequence of a PDE3B reference mRNA molecule is set forth in SEQ ID NO:2. The nucleotide sequence of another PDE3B reference mRNA molecule is set forth in SEQ ID NO:3. The nucleotide sequence of another PDE3B reference mRNA molecule is set forth in SEQ ID NO:4. The nucleotide sequence of a PDE3B reference mRNA molecule is set forth in SEQ ID NO:5. The nucleotide sequence of another PDE3B reference mRNA molecule is set forth in SEQ ID NO:6. The nucleotide sequence of another PDE3B reference mRNA molecule is set forth in SEQ ID NO:7. The nucleotide sequence of a PDE3B reference mRNA molecule is set forth in SEQ ID NO:8. The nucleotide sequence of another PDE3B reference mRNA molecule is set forth in SEQ ID NO:9. The nucleotide sequence of another PDE3B reference mRNA molecule is set forth in SEQ ID NO:10. The nucleotide sequence of another PDE3B reference mRNA molecule is set forth in SEQ ID NO:11.

The nucleotide sequence of a PDE3B reference cDNA molecule is set forth in SEQ ID NO:12. The nucleotide sequence of another PDE3B reference cDNA molecule is set forth in SEQ ID NO:13. The nucleotide sequence of another PDE3B reference cDNA molecule is set forth in SEQ ID NO:14. The nucleotide sequence of a PDE3B reference cDNA molecule is set forth in SEQ ID NO:15. The nucleotide sequence of another PDE3B reference cDNA molecule is set forth in SEQ ID NO:16. The nucleotide sequence of another PDE3B reference cDNA molecule is set forth in SEQ ID NO:17. The nucleotide sequence of another PDE3B reference cDNA molecule is set forth in SEQ ID NO:18. The nucleotide sequence of another PDE3B reference cDNA molecule is set forth in SEQ ID NO:19. The nucleotide sequence of a PDE3B reference cDNA molecule is set forth in SEQ ID NO:20. The nucleotide sequence of another PDE3B reference cDNA molecule is set forth in SEQ ID NO:21.

The amino acid sequence of a PDE3B reference polypeptide is set forth in SEQ ID NO:22. Referring to SEQ ID NO:22, the PDE3B reference polypeptide is 1,112 amino acids in length. The amino acid sequence of a PDE3B reference polypeptide is set forth in SEQ ID NO:23. Referring to SEQ ID NO:23, the PDE3B reference polypeptide is 1,061 amino acids in length. The amino acid sequence of a PDE3B reference polypeptide is set forth in SEQ ID NO:24. Referring to SEQ ID NO:24, the PDE3B reference polypeptide is 1,190 amino acids in length. The amino acid sequence of a PDE3B reference polypeptide is set forth in SEQ ID NO:25. Referring to SEQ ID NO:25, the PDE3B reference polypeptide is 298 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3XFLAG, 6Xhis or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit a liver disease or type 2 diabetes for use in the treatment of the liver disease or type 2 diabetes in a subject that is PDE3B reference or that has: a PDE3B predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide. Any of the therapeutic agents that treat or inhibit a liver disease or type 2 diabetes described herein can be used in these methods. For treating a PDE3B reference subject, the administered amount of therapeutic agents that treat or inhibit a liver disease or type 2 diabetes is greater than a standard dosage amount. For treating a subject that is heterozygous or homozygous as stated above, the administered amount of therapeutic agents that treat or inhibit a liver disease or type 2 diabetes is less than or the same as a standard dosage amount.

The present disclosure also provides therapeutic agents that treat or inhibit a liver disease or type 2 diabetes for use in the preparation of a medicament for treating a liver disease or type 2 diabetes in a subject that is PDE3B reference or that has: a PDE3B predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide. Any of the therapeutic agents that treat or inhibit a liver disease or type 2 diabetes described herein can be used in these methods. For treating a PDE3B reference subject, the administered amount of therapeutic agents that treat or inhibit a liver disease or type 2 diabetes is greater than a standard dosage amount. For treating a subject that is heterozygous or homozygous as stated above, the administered amount of therapeutic agents that treat or inhibit a liver disease or type 2 diabetes is less than or the same as a standard dosage amount.

The present disclosure also provides PDE3B inhibitors that treat or inhibit a liver disease or type 2 diabetes for use in the treatment of the liver disease or type 2 diabetes in a subject that is PDE3B reference or that is heterozygous for: a PDE3B predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide. Any of the PDE3B inhibitors described herein can be used in these methods.

The present disclosure also provides PDE3B inhibitors that treat or inhibit a liver disease or type 2 diabetes for use in the preparation of a medicament for treating a liver disease or type 2 diabetes in a subject that is PDE3B reference or that is heterozygous for: a PDE3B predicted loss-of-function or missense variant genomic nucleic acid molecule encoding a PDE3B polypeptide; a PDE3B predicted loss-of-function or missense variant mRNA molecule encoding a PDE3B polypeptide; or a PDE3B predicted loss-of-function or missense variant cDNA molecule encoding a PDE3B polypeptide. Any of the PDE3B inhibitors described herein can be used in these methods.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example: Loss of Function of the Gene Encoding PDE3B is Associated with Lower Liver Fat, and Lower Risk of Liver Injury, Liver Disease and Type 2 Diabetes Rare nonsynonymous variants in PDE3B have been associated with body fat distribution (Emdin et al., Nat. Commun., 2018, 9, 1613). Because the distribution of body fat is a risk factor for non-alcoholic fatty liver disease, it was hypothesized that rare nonsynonymous variants in this gene may be associated with deposition of fat in the liver and its associated disease outcomes, specifically type 2 diabetes and non-alcoholic fatty liver disease. To test this hypothesis, the associations with these health traits for predicted loss-of-function (pLOF) or predicted deleterious missense variants in PDE3B were estimated in over 500,000 people from multiple cohorts who underwent whole exome sequencing.

Table 3 shows the association with body mass index adjusted waist-to-hip ratio (BMI-adjusted WHR), a measure of fat distribution independent of overall adiposity, for the burden of rare (alternate allele frequency (AAF) <1%) pLOF variants (alone or in combination with predicted-deleterious missense variants) in PDE3B.

TABLE 3

The burden of loss of function or predicted deleterious missense variants of PDE3B is associated with lower BMI-adjusted WHR in UKB and MCPS

| Genetic exposure | Outcome | Per allele beta (95% confidence interval) in SD | P | Genotype counts, RR\|RA\|AA genotypes |
|---|---|---|---|---|
| pLOF; AAF <1% | BMI-adjusted WHR | −0.21 (−0.26, −0.16) | 3.90E−15 | 523,172\|1,298\|0 |

TABLE 3-continued

The burden of loss of function or predicted deleterious missense variants of PDE3B is associated with lower BMI-adjusted WHR in UKB and MCPS

| Genetic exposure | Outcome | Per allele beta (95% confidence interval) in SD | P | Genotype counts, RR\|RA\|AA genotypes |
|---|---|---|---|---|
| pLOF + deleterious missense; AAF <1% | BMI-adjusted WHR | −0.19 (−0.23, −0.15) | 7.80E−22 | 522,197\|2,273\|0 |

Note:
RR indicates the number of individuals in the population studies carrying no alternative alleles; RA indicates the number of individuals carrying one or more heterozygous alternative alleles; AA indicates the number of individuals carrying one or more homozygous alternative alleles; The genetic exposure (or effect allele), is the burden of rare allele causing loss of function (pLOF) or a predicted-deleterious missense variant with an alternative allele frequency less than 1% (AAF <1%).

Rare pLOF variants or pLOF plus deleterious missense variants in PDE3B were strongly associated with lower BMI-adjusted WHR, i.e. with a more favorable body fat distribution. The results show that pLOF variants and predicted deleterious missense variants combined are more strongly associated with fat distribution and have similar effect size compared to pLOF variants alone, indicating that the predicted-deleterious missense variants included in the analysis are likely conferring a loss of function. Hence, the combination of rare predicted loss of function variants and rare deleterious missense variants improves statistical power to study the consequences of genetic loss of function of PDE3B.

Associations with liver fat content, as measured by imaging and liver injury as measured by alanine aminotransferase (ALT), a liver enzyme used in clinical practice as a biomarker of liver injury, were estimated next. Liver fat content was measured by magnetic resonance imaging (MRI) derived proton density fat fraction (PDFF) of the liver. PDFF is defined as the ratio of density of mobile protons from fat (triglycerides) and the total density of protons from mobile triglycerides and mobile water and reflects the concentration of fat within a tissue. Circulating ALT levels indicate leakage from damaged cells due to inflammation or cell death. It was found that the burden of rare pLOF variants or pLOF and predicted deleterious missense variants in PDE3B is associated with lower PDFF and lower circulating ALT levels (Table 4).

TABLE 4

The burden of loss of function or predicted deleterious missense variants in PDE3B is associated with lower liver fat and lower liver damage, as measured by magnetic resonance imaging (MRI) derived proton density fat fraction (PDFF) of the liver and alanine aminotransferase (ALT), respectively

| Genetic exposure | Outcome | Per allele beta (95% confidence interval) | P | Genotype counts, RR\|RA\|AA genotypes |
|---|---|---|---|---|
| pLOF; AAF <1% | PDFF | −0.20 (−0.37, −0.02) | 0.02 | 36,662\|98\|0 |
| pLOF + deleterious missense; AAF <1% | PDFF | −0.16 (−0.29, −0.03) | 0.01 | 36,583\|177\|0 |

TABLE 4-continued

The burden of loss of function or predicted deleterious missense variants in PDE3B is associated with lower liver fat and lower liver damage, as measured by magnetic resonance imaging (MRI) derived proton density fat fraction (PDFF) of the liver and alanine aminotransferase (ALT), respectively

| Genetic exposure | Outcome | Per allele beta (95% confidence interval) | P | Genotype counts, RR\|RA\|AA genotypes |
|---|---|---|---|---|
| pLOF; AAF <1% | ALT | -0.10 (-0.15, -0.05) | 0.0001 | 516,941\|1,370\|0 |
| pLOF + deleterious missense; AAF <1% | ALT | -0.08 (-0.12, -0.04) | 3.4E-05 | 515,859\|2,452\|0 |

Note:
RR indicates the number of individuals in the population studies carrying no alternative alleles; RA indicates the number of individuals carrying one or more heterozygous alternative alleles; AA indicates the number of individuals carrying one or more homozygous alternative alleles; The genetic exposure (or effect allele), is the burden of rare allele causing loss of function (pLOF) or a predicted-deleterious missense variant with an alternative allele frequency less than 1% (AAF <1%).

These results constitute the first evidence linking loss of function of PDE3B with protection from liver fat deposition and liver damage in humans.

Furthermore, it was found that individuals carrying PDE3B loss of function variants and predicted deleterious missense variants have lower risk of developing chronic liver disease in a meta-analysis of multiple cohort studies (Table 5).

TABLE 5

The burden of loss of function or predicted deleterious missense variants of PDE3B is associated with lower odds of clinical diagnosis of liver disease in a meta-analysis of UKB, GHS, SINAI, MDCS and UPENN-PMBB. Associations with non-alcoholic steatohepatitis or liver fibrosis at liver biopsy were estimated in bariatric surgery participants from the GHS cohort

| Genetic exposure | Outcome | OR (95% confidence interval) | P | Genotype counts, RR\|RA\|AA genotypes |
|---|---|---|---|---|
| pLOF; AAF <1% | Non alcoholic liver disease | 0.70 (0.50, 1.00) | 0.04 | Cases: 14,875\|24\|0 Controls: 445,329\|1,226\|0 |
| pLOF + deleterious missense; AAF <1% | Non alcoholic liver disease | 0.78 (0.60, 1.02) | 0.07 | Cases: 14,847\|52\|0 Controls: 444,402\|2,153\|0 |
| pLOF; AAF <1% | Parenchymal Liver Disease | 0.72 (0.51, 1.00) | 0.04 | Cases: 17,020\|28\|0 Controls: 439,215\|1,171\|0 |
| pLOF + deleterious missense; AAF <1% | Parenchymal Liver Disease | 0.81 (0.64, 1.03) | 0.08 | Cases: 16,986\|62\|0 Controls: 438,269\|2,117\|0 |
| pLOF; AAF <1% | Non-alcoholic steatohepatitis or liver fibrosis at liver biopsy in a bariatric surgery cohort from the GHS study | 0.09 (0.01, 1.12) | 0.06 | Cases: 1,395\|3\|0 Controls: 772\|5\|0 |
| pLOF + deleterious missense; AAF <1% | Non-alcoholic steatohepatitis or liver fibrosis at liver biopsy in a bariatric surgery cohort from the GHS study | 0.17 (0.03, 1.01) | 0.05 | Cases: 1,396\|2\|0 Controls: 774\|3\|0 |

Note:
RR indicates the number of individuals in the population studies carrying no alternative alleles; RA indicates the number of individuals carrying one or more heterozygous alternative alleles; AA indicates the number of individuals carrying one or more homozygous alternative alleles; The genetic exposure (or effect allele), is the burden of rare allele causing loss of function (pLOF) or a predicted-deleterious missense variant with an alternative allele frequency less than 1% (AAF <1%); OR indicates odds ratio for the effect allele.

In addition, the results shown an association with lower risk of non-alcoholic steatohepatitis or liver fibrosis in bariatric surgery patients in the GHS study (Table 7). These results constitute the first evidence linking loss of function of PDE3B with protection from chronic liver diseases in humans.

Furthermore, the analyses reveal that carriers of PDE3B loss of function variants and predicted deleterious missense variants have lower risk of type 2 diabetes as shown in Table 6.

TABLE 6

The burden of loss of function or predicted deleterious missense variants of PDE3B is associated with lower risk of type 2 diabetes in a meta-analysis of UKB and GHS

| Genetic exposure | Outcome | OR (95% confidence interval) | P | Genotype counts, RR\|RA\|AA genotypes |
|---|---|---|---|---|
| pLOF; AAF <1% | Type 2 diabetes | 0.78 (0.64, 0.95) | 0.01 | Cases: 53,965\|106\|0 Controls: 483,255\|1,330\|0 |
| pLOF + deleterious missense; AAF <1% | Type 2 diabetes | 0.77 (0.66, 0.89) | 0.0003 | Cases: 53,868\|203\|0 Controls: 482,207\|2,378\|0 |

Note:
RR indicates the number of individuals in the population studies carrying no alternative alleles; RA indicates the number of individuals carrying one or more heterozygous alternative alleles; AA indicates the number of individuals carrying one or more homozygous alternative alleles; The genetic exposure (or effect allele), is the burden of rare allele causing loss of function (pLOF) or a predicted-deleterious missense variant with an alternative allele frequency less than 1% (AAF <1%); OR indicates odds ratio for the effect allele.

These results constitute the first evidence linking loss of function of PDE3B with protection from type 2 diabetes in humans.

Participating Cohorts

Genetic association studies were performed in the United Kingdom Biobank (UKB) cohort (Sudlow et al., PLoS Med, 2015, 12, e1001779) and the DiscoverEHR cohort from the Geisinger Health System (GHS) MyCode Community Health Initiative (Carey et al., Genet. Med., 2016, 18, 906-13). UKB is a population-based cohort study of people aged between 40 and 69 years recruited through 22 testing centers in the UK between 2006-2010. Over 430,000 European ancestry participants from UKB with available whole-exome sequencing and clinical phenotype data were included. The GHS MyCode study Community Health Initiative is a health system-based cohort of patients from Central and Eastern Pennsylvania (USA) recruited in 2007-2019. Over 130,000 European ancestry participants from GHS with available whole-exome sequencing and clinical phenotype data were included. The associations between PDE3B and waist hip ratio were estimated in UKB and the Mexico City Prospective Study (MCPS; Int. J. Epidemiol., 2006, 35, 243-9). The associations with liver outcomes also included the Mount Sinai BioMe Biobank cohort (SINAI, Cell, 2019, 177, 58-69), The University of Pennsylvania Penn Medicine BioBank (UPENN-PMBB; Park et al., 2020, doi:10.1038/s41436-019-0625-8) and Malmo Diet and Cancer Study (MDCS) a Swedish population-based, prospective, observational cohort recruited between 1991 and 1996 (Berglund et al., 1993, doi:10.1111/j.1365-2796.1993.tb00647.x).

Phenotype Definitions

Clinical laboratory measurements for ALT was extracted from electronic health records (EHRs) of participants from GHS. Median values were calculated for all participants with two or more measurements. In UKB, ALT was measured by IFCC (International Federation of Clinical Chemistry) analysis on a Beckman Coulter AU5800 at the baseline visit of the study; Hb1Ac was measured by HPLC using a Bio-Rad VARIANT II Turbo. BMI was calculated by dividing weight in kilograms by the square of height in meters. Waist-to-hip ratio was calculated by dividing waist circumference by hip circumference. Prior to genetic association analysis, continuous phenotype values were transformed by the inverse standard normal function, applied within each ancestry group and separately in men and women.

Disease outcomes were defined according to the International Classification of Diseases, Ninth and Tenth Revision (ICD-9 and ICD-10) using EHRs and self-reports when available and combined into single variables. Individuals with type 2 diabetes were identified using a previously described algorithm (Lotta et al., JAMA, 2018, doi: 10.1001/jama.2018.19329), chronic liver diseases were defined according to definitions listed in Table 7. Individuals with non-alcoholic liver disease and parenchymal liver disease were identified in UKB, GHS, SINAI, UPENN-PMBB and MALMO; individuals with type 2 diabetes were identified in UKB and GHS.

TABLE 7

Definitions of liver disease outcomes

| Liver disease outcome | Case definition | Controls definition |
|---|---|---|
| Non-alcoholic liver disease | ICD10: K721, K740, K741, K742, K746, K758, K760 | ICD10: K70, K71, K72, K73, K74, K75, K76, K77, I81, I85, I982, I983, I864, T864, Z944, C220 OPCS4: G10, G144, J01 f.20002: 1604, 1158, 1141 ALT: >33 IU/L for men and >24 IU/L for women |
| Parenchymal liver disease | ICD10: K70, K71, K72, K73, K74, K753, K753, K752, K754, K758, K759, K760, K767, K7681 OPCS4: G10, G144, J01 UKB.f.20002: 1604, 1158, 1141 | ICD10: K70, K71, K72, K73, K74, K75, K76, K77, I81, I85, I982, I983, I864, T864, Z944, C220 OPCS4: G10, G144, J01 f.20002: 1604, 1158, 1141 ALT: >33 IU/L for men and >24 IU/L for women |

Note:
ICD10 indicates the 10th revision of the International Statistical Classification of Diseases and Related Health Problems; UKB.OPCS4 indicates Office of Population Censuses and Surveys (OPCS) Classification of Interventions and Procedures version 4 as used in the UK Biobank (UKB); UKB.f.20002 indicates self-reported non-cancer illness codes as used in UKB. UKB.f.20004 indicates self-reported medical procedures as used in UKB.

Liver histopathologic phenotype definitions in the GHS bariatric surgery cohort

Wedge biopsies of the liver were obtained intraoperatively during bariatric surgery in 3,779 individuals. The biopsies were consistently obtained 10 cm to the left of falciform ligament prior to any liver retraction or surgery on the stomach. The biopsy was divided into sections, with the primary section delivered to the clinical pathologists for liver histology (fixed in 10% neutral buffered formalin and stained with hematoxylin and eosin for routine histology and Masson's trichrome for assessment of fibrosis) and remaining sections stored within a research biobank (frozen in RNAlater and/or liquid nitrogen). Liver histology was conducted by an experienced pathologist and subsequently re-reviewed by a second experienced pathologist using the NASH Clinical Research Network scoring system as follows: steatosis grade 0 (67%); lobular inflammation grade 0 (no foci), grade 1 (mild, 4 foci per 200×field); fibrosis stage 0 (none), stage 1 (perisinusoidal or periportal fibrosis), stage 2 (perisinusoidal and periportal fibrosis), stage 3 (bridging fibrosis), and stage 4 (cirrhosis). These histologic diagnoses were used to define the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage); 4) Fibrosis: Any presence of fibrosis (regardless of stage).

Genotype Data

High coverage whole exome sequencing was performed as previously described (Science, 2016, 354:aaf6814; and Nature, 2020, 586, 749-756) and as summarized below. NimbleGen probes (VCRome; for part of the GHS cohort) or a modified version of the xGen design available from Integrated DNA Technologies (IDT; for the rest of GHS and other cohorts) were used for target sequence capture of the exome. A unique 6 base pair (bp) barcode (VCRome) or 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina v4 HiSeq 2500 (for part of the GHS cohort) or NovaSeq (for the rest of GHS and other cohorts) instruments. Sequencing had a coverage depth (i.e., number of sequence-reads covering each nucleotide in the target areas of the genome) sufficient to provide greater than 20×coverage over 85% of targeted bases in 96% of VCRome samples and 20×coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling was performed using the GLNexus system (DOI: 10.1101/343970). Variant mapping and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LOF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Adzhubei et al., Nat. Methods, 2010, 7, 248-9) and Polyphen2_HVAR (Adzhubei et al., Nat. Methods, 2010, 7, 248-9), LRT (Chun et al., Genome Res., 2009, 19, 1553-61) and MutationTaster (Schwarz et al., Nat. Methods, 2010, 7, 575-6). For each gene, the alternative allele frequency (AAF) and functional annotation of each variant determined inclusion into these 7 gene burden exposures: 1) pLOF variants with AAF <1%; 2) pLOF or missense variants predicted deleterious by 5/5 algorithms with AAF <1%.

Association analysis of gene burden of rare loss of function variation

Association between the burden of rare predicted loss-of-function or missense variants in a given gene and phenotype was tested by fitting a linear (for quantitative traits) or firth bias-corrected logistic (for binary traits) regression model adjusted for a polygenic score that approximates a genomic kinship matrix using REGENIE v1.0 (doi: doi.org/10.1101/2020.06.19.162354). Analyses were stratified by ancestry and adjusted for age, $age^2$, sex, age-by-sex and $age^2$-by-sex interaction terms, experimental batch-related covariates, 10 common variant-derived principal components, and 20 rare variant-derived principal components. Results across cohorts for each variant-phenotype association were combined using fixed effects inverse variance weighted meta-analysis. In gene burden tests, all individuals are labeled as heterozygotes if they carry one or more qualifying rare variant (as described above based on frequency and functional annotation) and as homozygotes if they carry any qualifying variant in the homozygous state. This "composite genotype" is then used to test for association.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

SEQUENCE LISTING

The patent contains a lengthy sequence listing. A copy of the sequence listing is available in electronic form from the USPTO web site (https://seqdata.uspto.gov/?pageRequest=docDetail&DocID=US12123001B2). An electronic copy of the sequence listing will also be available from the USPTO upon request and payment of the fee set forth in 37 CFR 1.19(b)(3).

What is claimed is:

1. A method of treating a human subject having a liver disease or type 2 diabetes, the method comprising administering a Phosphodiesterase 3B (PDE3B) inhibitor to the subject,
    wherein the PDE3B inhibitor comprises an antisense nucleic acid molecule, a small interfering RNA (siRNA), or a short hairpin RNA (shRNA) that hybridizes to a PDE3B mRNA, and
    wherein the subject is PDE3B reference or heterozygous for a PDE3B predicted loss-of-function or missense variant nucleic acid molecule.

2. The method according to claim 1, wherein the liver disease is a fatty liver disease, hepatocellular carcinoma, liver cirrhosis, liver fibrosis, simple steatosis, steatohepatitis, or non-alcoholic steatohepatitis (NASH).

3. The method according to claim 2, wherein the fatty liver disease is alcoholic fatty liver disease (AFLD) or nonalcoholic fatty liver disease (NAFLD).

4. The method according to claim 1, wherein when the subject is PDE3B reference or when the subject is heterozygous for a PDE3B predicted loss-of-function or missense variant, the subject is also administered a therapeutic agent that treats or inhibits a liver disease or type 2 diabetes.

5. The method according to claim 1, wherein the PDE3B predicted loss-of-function or missense variant nucleic acid molecule is a splice-site variant, a stop-gain variant, a start-loss variant, a stop-loss variant, a frameshift variant, or an in-frame indel variant, or a variant that encodes a truncated PDE3B polypeptide.

6. The method according to claim 5, wherein the PDE3B predicted loss-of-function or missense variant nucleic acid molecule encodes a truncated PDE3B polypeptide.

7. A method of treating a human subject with a therapeutic agent that treats or inhibits a liver disease or type 2 diabetes, wherein the subject is suffering from a liver disease or type 2 diabetes, the method comprising the steps of:
   determining whether the subject has a Phosphodiesterase 3B (PDE3B) predicted loss-of-function or missense variant nucleic acid molecule encoding a human PDE3B polypeptide by:
      obtaining or having obtained a biological sample from the subject; and
      performing or having performed a sequence analysis on the biological sample to determine if the subject has a genotype comprising the PDE3B predicted loss-of-function or missense variant nucleic acid molecule; and
   when the subject is PDE3B reference, then administering or continuing to administer to the subject the therapeutic agent that treats or inhibits the liver disease or type 2 diabetes in an amount that is greater than a standard dosage amount, and administering to the subject a PDE3B inhibitor; and
   when the subject is heterozygous for a PDE3B predicted loss-of-function or missense variant nucleic acid molecule, then administering or continuing to administer to the subject the therapeutic agent that treats or inhibits the liver disease or type 2 diabetes in an amount that is the same as or less than a standard dosage amount, and administering to the subject a PDE3B inhibitor;
   when the subject is homozygous for a PDE3B predicted loss-of-function or missense variant nucleic acid molecule, then administering or continuing to administer to the subject the therapeutic agent that treats or inhibits the liver disease or type 2 diabetes in an amount that is the same as or less than a standard dosage amount;
   wherein the presence of a genotype having the PDE3B predicted loss-of-function or missense variant nucleic acid molecule encoding the human PDE3B polypeptide indicates the subject has a decreased risk of developing the liver disease or type 2 diabetes; and
   wherein the PDE3B inhibitor comprises an antisense nucleic acid molecule, a small interfering RNA (siRNA), or a short hairpin RNA (shRNA) that hybridizes to a PDE3B mRNA.

8. The method according to claim 7, wherein the subject is PDE3B reference, and the subject is administered or continued to be administered the therapeutic agent that treats or inhibits the liver disease or type 2 diabetes in an amount that is greater than a standard dosage amount, and is administered a PDE3B inhibitor.

9. The method according to claim 7, wherein the subject is heterozygous for a PDE3B predicted loss-of-function or missense variant, and the subject is administered or continued to be administered the therapeutic agent that treats or inhibits the liver disease or type 2 diabetes in an amount that is the same as or less than a standard dosage amount, and is administered a PDE3B inhibitor.

10. The method according to claim 7, wherein the predicted loss-of-function or missense variant PDE3B nucleic acid molecule is a splice-site variant, a stop-gain variant, a start-loss variant, a stop-loss variant, a frameshift variant, or an in-frame indel variant, or a variant that encodes a truncated PDE3B polypeptide.

11. The method according to claim 7, wherein the predicted loss-of-function or missense variant PDE3B nucleic acid molecule encodes a truncated PDE3B polypeptide.

12. The method according to claim 7, wherein the therapeutic agent for treating type 2 diabetes is chosen from metformin, insulin, glyburide, glipizide, glimepiride, repaglinide, nateglinide, rosiglitazone pioglitazone, sitagliptin, saxagliptin, linagliptin, exenatide, liraglutide, semaglutide, canagliflozin, dapagliflozin, and empagliflozin, or any combination thereof.

13. The method according to claim 7, wherein the therapeutic agent for treating liver disease is chosen from disulfiram, naltrexone, acamprosate, prednisone, azathioprine, an interferon, a protease inhibitor, a reverse transcriptase inhibitor, penicillamine, trientine, deferoxamine, bumetanide, furosemide, hydrochlorothiazide, chlorothiazide, amiloride, triamterene, spironolactone, atenolol, metoprolol, nadolol, propranolol, timolol, and carvedilol, or any combination thereof.

14. The method according to claim 7, wherein the liver disease is steatosis, steatohepatitis, or NASH, and the therapeutic agent is chosen from obeticholic acid, selonsertib, elafibranor, cenicriviroc, GR-MD-02, MGL-3196, IMM-124E, arachidyl amido cholanoic acid, GS-0976, emricasan, volixibat, NGM282, GS-9674, tropifexor, MN-001, LMB763, BI-1467335, MSDC-0602, PF-05221304, saroglitazar, BMS-986036, lanifibranor, semaglutide, nitazoxanide, GRI-0621, EYP001, VK2809, nalmefene, LIK066, MT-3995, elobixibat, namodenoson, foralumab, SAR425899, sotagliflozin, EDP-305, isosabutate, gemcabene, TERN-101, KBP-042, PF-06865571, DUR-928, PF-06835919, NGM313, BMS-986171, namacizumab, CER-209, ND-L02-s0201, RTU-1096, DRX-065, IONIS-DGAT2Rx, INT-767, NC-001, seladepar, PXL770, TERN-201, NV556, AZD2693, SP-1373, VK0214, TGFTX4, RLBN1127, GKT137831, RYI-018, CB4209, CB4211, and JH-0920, or any combination thereof.

* * * * *